US012178864B2

(12) United States Patent
Wright et al.

(10) Patent No.: US 12,178,864 B2
(45) Date of Patent: Dec. 31, 2024

(54) TRYPANOSOMAL VACCINE

(71) Applicant: GENOME RESEARCH LIMITED (GB/GB), Saffron Walden (GB)

(72) Inventors: Gavin Wright, Saffron Walden (GB); Delphine Autheman, Saffron Walden (GB)

(73) Assignee: GENOME RESEARCH LIMITED, Saffron Walden (GB)

( * ) Notice: Subject to any disclaimer, the term of this patent is extended or adjusted under 35 U.S.C. 154(b) by 763 days.

(21) Appl. No.: 17/420,993

(22) PCT Filed: Jan. 7, 2020

(86) PCT No.: PCT/GB2020/050023

§ 371 (c)(1),
(2) Date: Jul. 6, 2021

(87) PCT Pub. No.: WO2020/144465

PCT Pub. Date: Jul. 16, 2020

(65) Prior Publication Data

US 2022/0088161 A1 Mar. 24, 2022

(30) Foreign Application Priority Data

Jan. 7, 2019 (GB) ..................................... 1900192

(51) Int. Cl.
*A61K 39/005* (2006.01)
*A61P 33/02* (2006.01)
*A61K 39/00* (2006.01)

(52) U.S. Cl.
CPC ............ *A61K 39/005* (2013.01); *A61P 33/02* (2018.01); *A61K 2039/55577* (2013.01)

(58) Field of Classification Search
None
See application file for complete search history.

(56) References Cited

U.S. PATENT DOCUMENTS

2017/0296637 A1 10/2017 Pleguezuelos Mateo et al.
2018/0185461 A1 7/2018 Vincendeau et al.

FOREIGN PATENT DOCUMENTS

WO WO 2016/185135 A1 11/2016
WO WO 2017/187179 A1 11/2017
WO WO 2020/144464 A1 7/2020
WO WO 2020/144465 A1 7/2020

OTHER PUBLICATIONS

Black and Mansfield "Prospects for vaccination against pathogenic African trypanosomes", Parasite Immunol., vol. 38, No. 12, pp. 735-743 (2016).

Database Uniprot (Online), Protein—Uncharacterized Protein, gene—YvY486_0003730 , Organism—*Trypanosoma vivax* (strain Y486), Database accession No. Uniprot: F9WUZ3, Last modified Oct. 19, 2011.

Fleming et al., "Proteomic Identification of Immunodiagnostic Antigens for Trypanosoma vivax Infections in Cattle and Generation of a Proof-of-Concept Lateral Flow Test Diagnostic Device", PLoS Negl. Trop. Dis., vol. 10, No. 9, Article e0004977, 11 pages (2016)..

GenBank Accession No. CCD21393.1, "Hypothetical protein, conserved in T. vivax [*Trypanosoma vivax* Y486]" NCBI, 1 page, Aug. 8, 2011.

Greif et al., "Transcriptome analysis of the bloodstream stage from the parasite *Trypanosoma vivax*", BMC Genomics, vol. 14, No. 149, 17 pages (2013).

Guedes et al., "A comparative in silico linear B-cell epitope prediction and characterization for South American and African Trypanosoma vivax strains", Genomics, vol. 111, No. 3, pp. 407-417 (2019).

International Search Report from International Application No. PCT/GB2020/050022, 6 pages, ISR Mailed May 14, 2020, application now published as International Publication No. WO2020/144464, published on Jul. 16, 2020.

International Search Report from International Patent Application No. PCT/GB2020/050023, 4 pages, mailed Mar. 20, 2020, application now published as International Publlication No. WO2020/144465 on Jul. 16, 2020.

Jackson et al., "Antigenic diversity is generated by distinct evolutionary mechanisms in African *trypanosome* species", Proc. Natl. Acad. Sci. U.S.A. vol. 109, No. 9, pp. 3416-3421 (2012).

Jackson et al., "Global Gene Expression Profiling through the Complete Life Cycle of Trypanosoma vivax", PLOS Neglected Tropical diseases, vol. 9, No. 8, J. e0003975, 29 pages (2015).

Li et al., "Immunization with recombinant beta-tubulin from Trypanosoma evansi induced protection against T. evansi, T. equiperdum and T. b. brucei infection in mice", Parasite Immunol., vol. 29, No. 4, pp. 191-199 (2007).

UniParc, "UPI000218C98C", UniProt, Organism: *Trypanosoma vivax* (strain Y486), Sequence UPI000218C98C, First Seen Oct. 19, 2011.

Ziegelbauer and Overath, "Organization of two invariant surface glycoproteins in the surface coat of Trypanosoma brucei", Infect. Immun., vol. 61, No. 11, pp. 4540-4545 (1993).

*Primary Examiner* — Jennifer E Graser
(74) *Attorney, Agent, or Firm* — McDermott Will & Emery LLP; Judy M. Mohr; Brennen P. Baylor

(57) ABSTRACT

The invention relates to a trypanosomalvaccine, to pharmaceutical compositions comprising said vaccine and to their uses in vaccination to prevent trypanosomal infection in a mammal.

19 Claims, 14 Drawing Sheets

Specification includes a Sequence Listing.

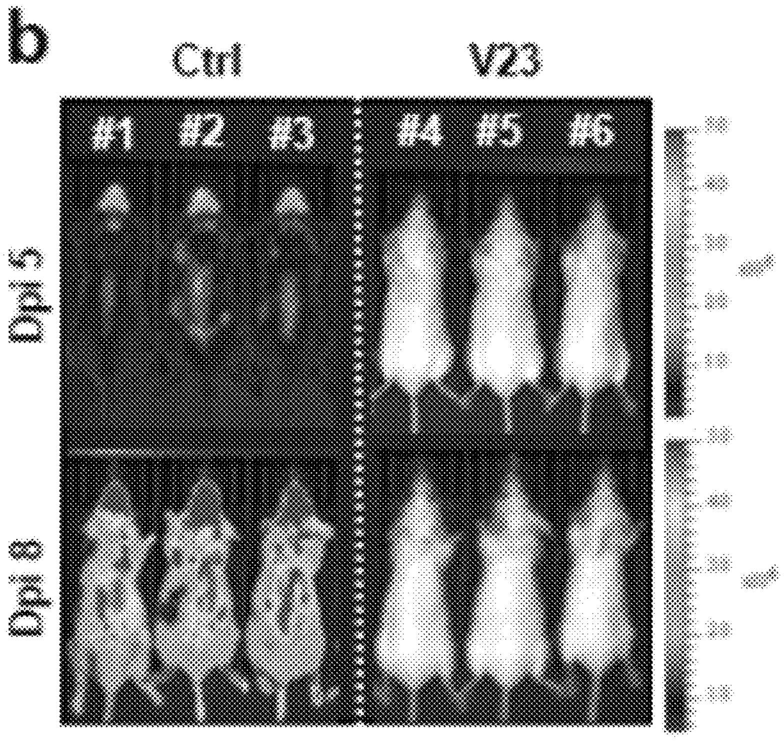
c
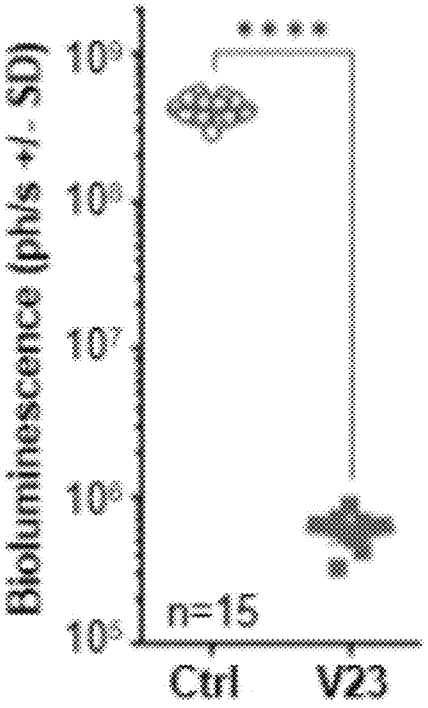
FIGURE 4 (ctd)

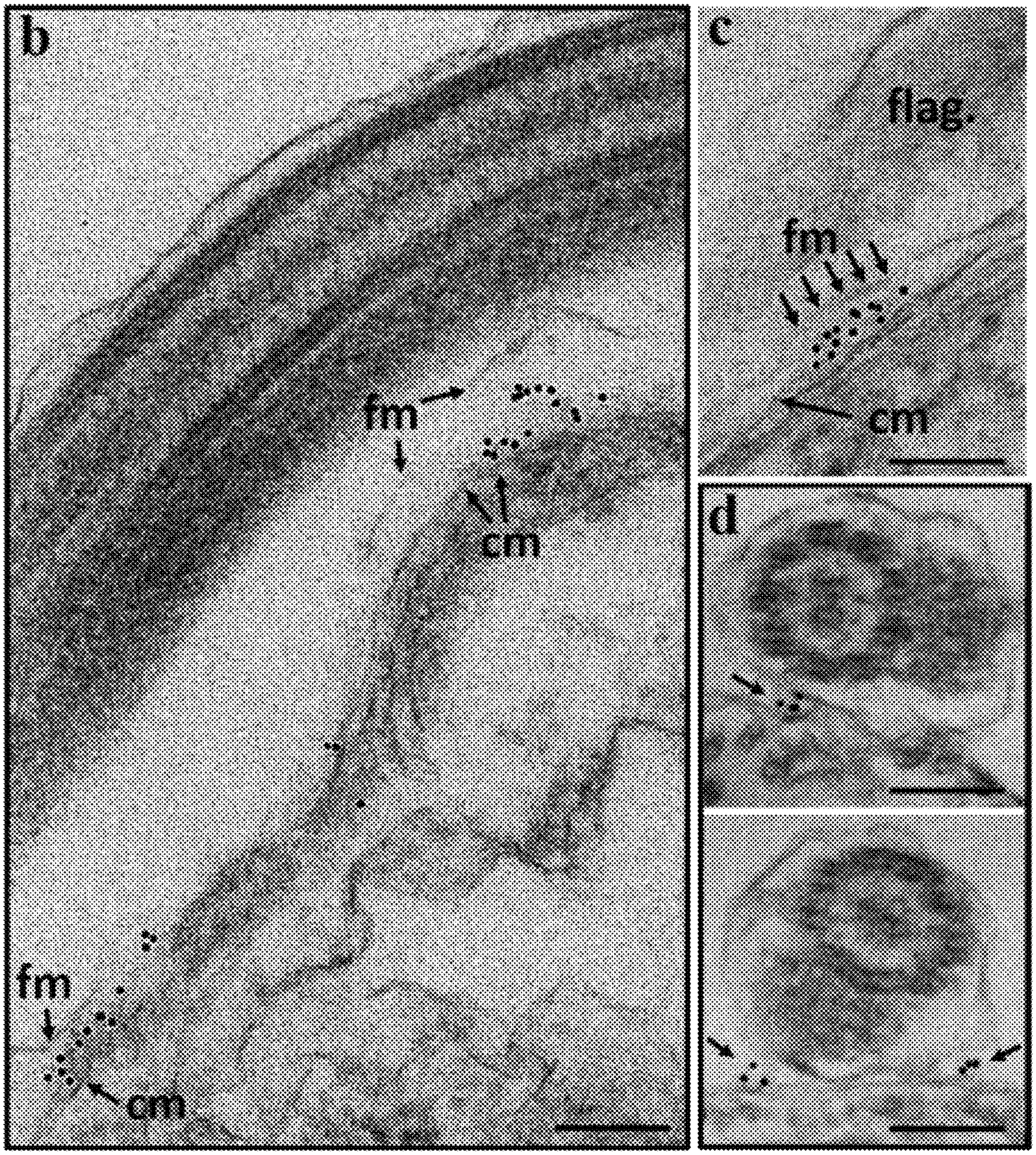
FIGURE 5 (ctd)

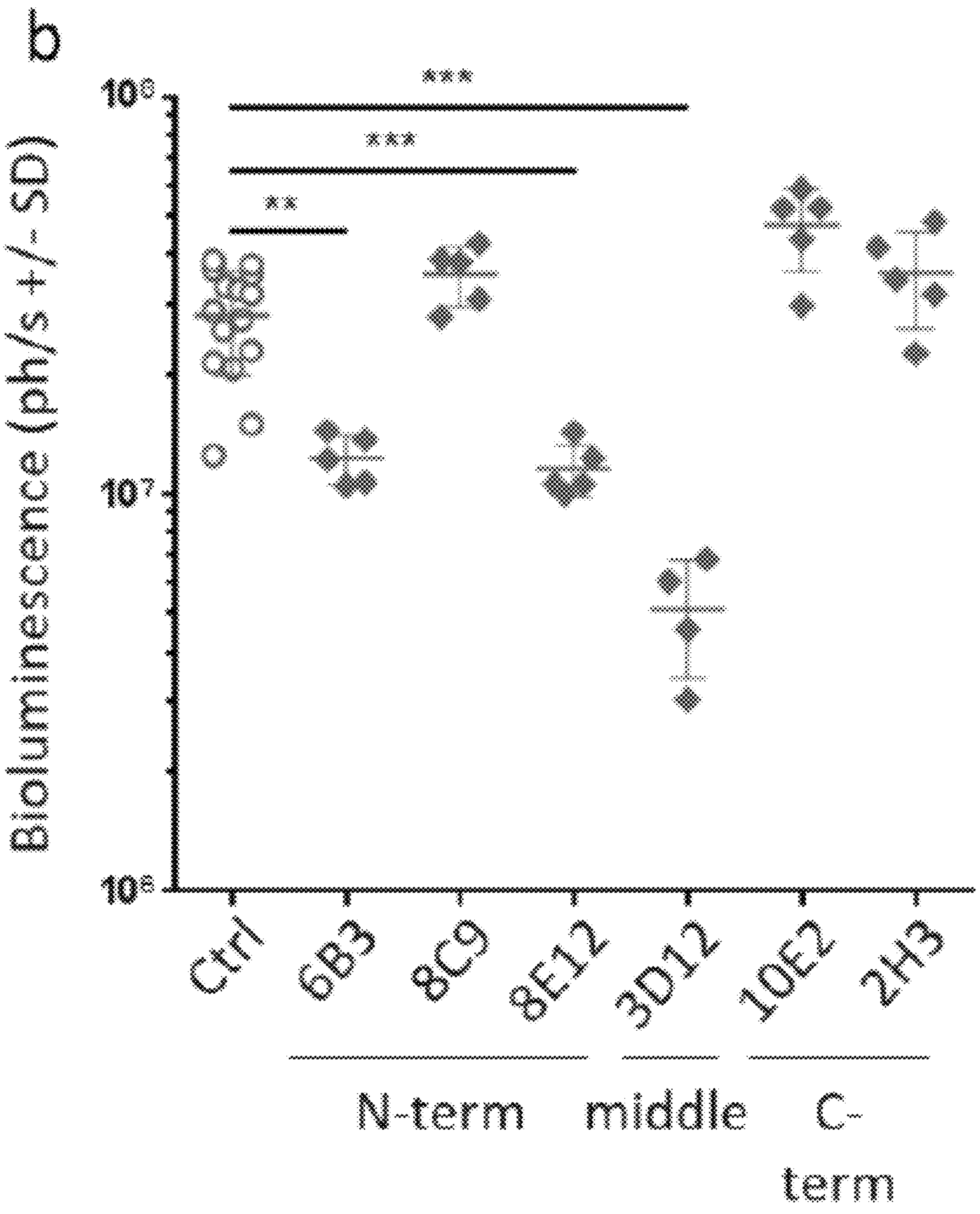
FIGURE 6 (ctd)

C
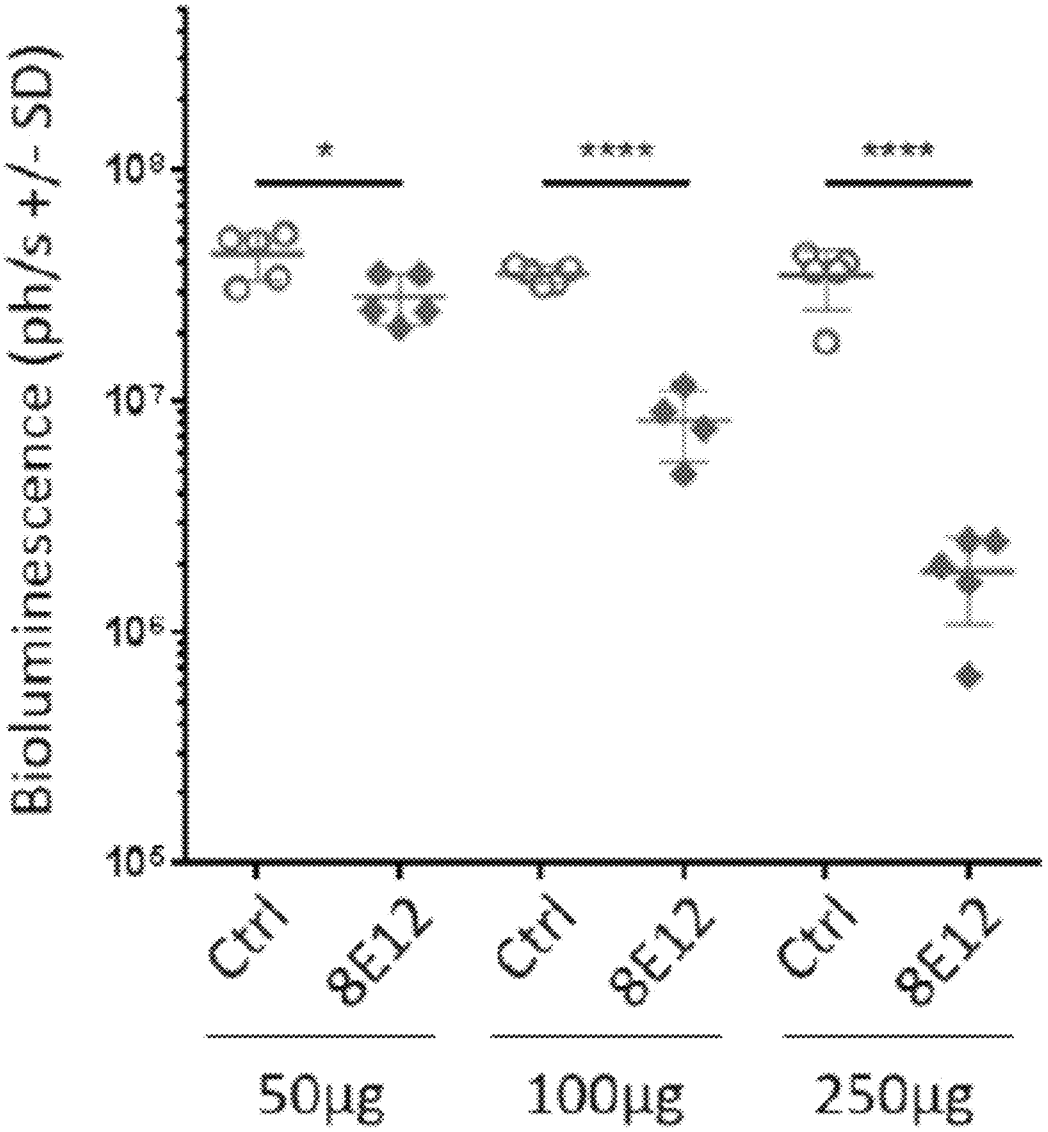
FIGURE 6 (ctd)

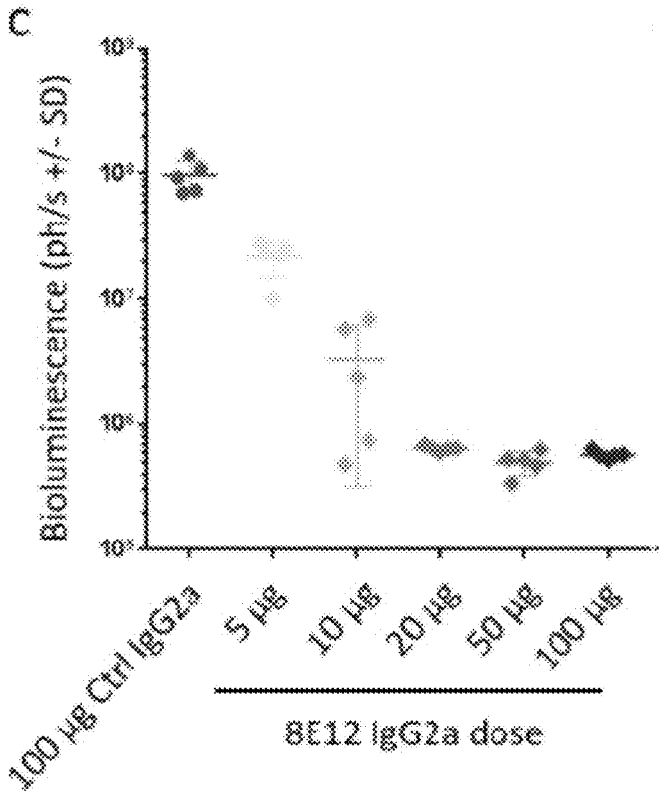
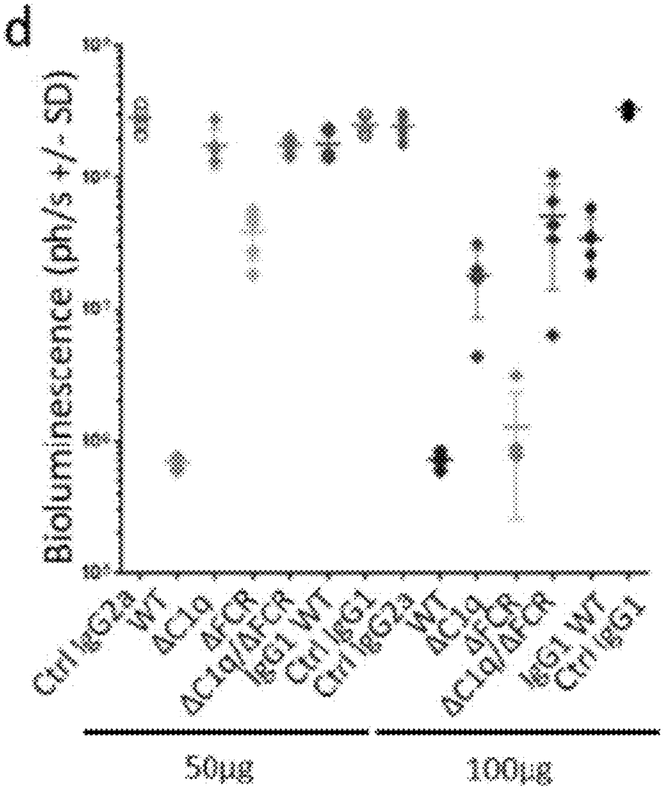
FIGURE 7 (ctd)

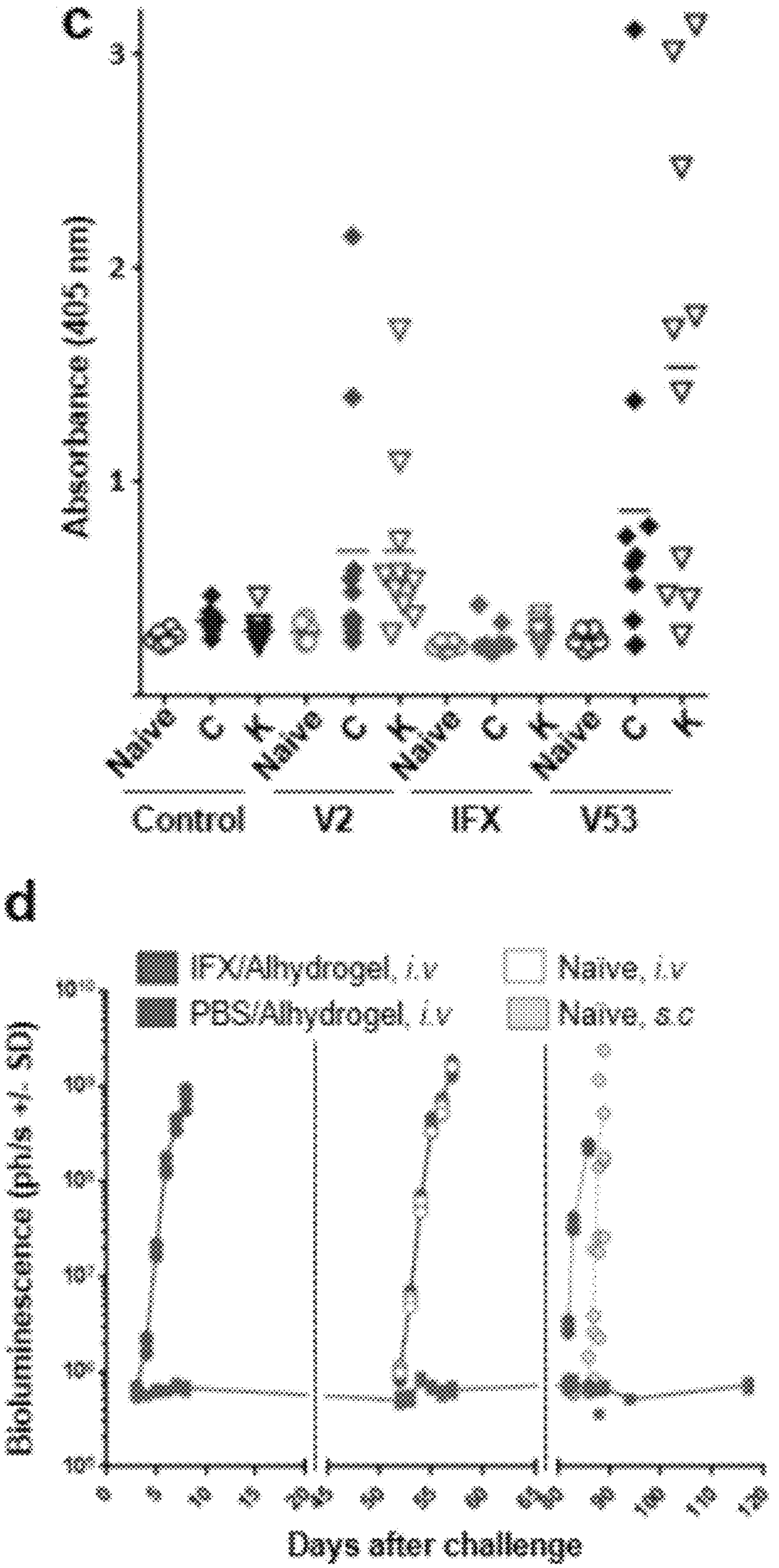
FIGURE 8 (ctd)

SEQUENCE LISTING

```
<160> NUMBER OF SEQ ID NOS: 6

<210> SEQ ID NO 1
<211> LENGTH: 532
<212> TYPE: PRT
<213> ORGANISM: T. vivax

<400> SEQUENCE: 1

Met Arg Cys His Glu Pro Pro Thr Pro Pro Gln Leu Ser Ala Thr Cys
1               5                   10                  15

Cys Val Ala Glu Glu Ile Asp Thr Tyr Asn Lys His Leu Asp Ala Leu
            20                  25                  30

Met Gln Ile Ile Gly Asp Ala Ile Lys Asn Ile Ser Thr Asn Glu Asp
        35                  40                  45
```

-continued

```
Asn Ala Arg Ala Arg Ala Glu Gly Leu Lys Gly Cys Asn Leu His Tyr
    50                  55                  60

Val Gln Phe Ala Val Ala His Thr Glu Gly Ser Val Val Ala Ala Arg
65                  70                  75                  80

Arg Glu Ala Val Lys Ala Gln Asn Thr Ile Lys Gly Ser Thr Ser Leu
                85                  90                  95

Leu Lys Lys Val Thr Ile Asp Ile Ser Asn Ser Phe Arg Asn Ile Ser
            100                 105                 110

Ser Lys Cys Asn Glu Leu Arg Glu Lys Tyr Pro Ser Leu Ile Pro Ala
        115                 120                 125

Asp Lys Asn Ser Pro Pro Asn Ile Thr Phe Lys Lys Ala Val Gln Leu
    130                 135                 140

Tyr Val Lys Asn Phe Ser Thr Cys Asn Val Met Tyr Ala Lys Lys Leu
145                 150                 155                 160

Leu Arg Leu Val Ala Gln Ser Glu Lys Ile Glu Ala Glu Val Ser Arg
                165                 170                 175

Ala Val Glu Arg Thr Asn Ala Ser Thr Met Glu Leu Ala Lys Leu Asp
            180                 185                 190

Lys Val Ala Val Gln Leu Asn Lys Asp Ile Thr Ser Asn Arg Thr Trp
        195                 200                 205

Ala Gly Cys Lys Leu Ala Glu Tyr His Gly Gln Met Asn Phe Val Phe
    210                 215                 220

Met Gly Phe Tyr Val Leu Leu Ser Asp Ile Leu Asp Glu Leu His Ser
225                 230                 235                 240

Leu Leu Lys Lys Ser Lys Ser Met Gln Pro Thr Arg Leu Thr Gln Glu
                245                 250                 255

Glu Val Arg Arg Ala Leu Ser Lys Ala Glu Gln Val Cys His Asp Val
            260                 265                 270

Ser Arg Phe Val Lys Ser Leu Gly Ser Thr Leu Arg Asp Phe Thr Asn
        275                 280                 285

Phe Val His Arg Leu Arg Lys Glu Tyr Leu His Gly Ile Leu Arg Asn
    290                 295                 300

Ala Ser Gly Phe Arg Glu Ser Phe Glu Arg Cys Tyr Lys Val Ala Thr
305                 310                 315                 320

Asn Asn Ser Val Thr Arg Leu Glu Ser Thr Val Glu Glu Ile Thr Ala
                325                 330                 335

Asn Asn Glu Asn Ile Ala Ala Trp Glu Ser Met Thr Val His Gln Trp
            340                 345                 350

Lys Asp Val Ser Lys Lys Leu Arg Gln Ser Leu Leu Thr Val Leu Gly
        355                 360                 365

Gly Ser Asn Glu Tyr Ile Leu Leu Tyr Gly Tyr Phe Gln Glu Phe Asp
    370                 375                 380

Ser Met Ser Val Arg Glu Phe Ser Asn Thr Val Arg Ala Phe Arg Gln
385                 390                 395                 400

Ser Ile Thr Glu Met Ser Val Ala Arg Asn Val Val Gly Val Ala Ala
                405                 410                 415

Lys Thr Val Ala Ala Asp Arg Lys Arg Ile Leu Cys Arg Ser Val Leu
            420                 425                 430

Met Phe Asn Lys Gly Thr Ala Gly Ser Glu Ser Ala Arg Lys Leu Tyr
        435                 440                 445

Glu Leu Cys Lys Thr Arg Met Pro Val Glu Glu Pro Asp Ser Ser Arg
    450                 455                 460
```

```
Glu Asp Gly Val Val Gly Thr Ser Gly Ser Glu Glu Glu Ile Ser Gly
465                 470                 475                 480

Lys Asp Gly Gly Thr Ser Phe Ser Val Ser Asp Ala Asp Tyr Trp Glu
                485                 490                 495

Trp Asp Val Pro Pro Lys Val Leu Glu Glu Ser Ser Gly Asp Leu Leu
            500                 505                 510

Tyr Asp Thr Ala Val Asp Leu His Thr Lys Arg Lys Ser Pro Phe Tyr
        515                 520                 525

Gln Val Gly Ser
    530


<210> SEQ ID NO 2
<211> LENGTH: 607
<212> TYPE: PRT
<213> ORGANISM: T. vivax

<400> SEQUENCE: 2

Met Glu Val Met Leu Phe Asp Tyr Phe His Val Leu Pro Ile Ser Cys
1               5                   10                  15

Lys Pro Arg Asn Phe Cys Ile Ala Phe Met Leu Met Phe Leu Arg Phe
            20                  25                  30

Cys Pro Val Phe Ala Met Arg Cys His Glu Pro Pro Thr Pro Pro Gln
        35                  40                  45

Leu Ser Ala Thr Cys Cys Val Ala Glu Glu Ile Asp Thr Tyr Asn Lys
    50                  55                  60

His Leu Asp Ala Leu Met Gln Ile Ile Gly Asp Ala Ile Lys Asn Ile
65                  70                  75                  80

Ser Thr Asn Glu Asp Asn Ala Arg Ala Arg Ala Glu Gly Leu Lys Gly
                85                  90                  95

Cys Asn Leu His Tyr Val Gln Phe Ala Val Ala His Thr Glu Gly Ser
            100                 105                 110

Val Val Ala Ala Arg Arg Glu Ala Val Lys Ala Gln Asn Thr Ile Lys
        115                 120                 125

Gly Ser Thr Ser Leu Leu Lys Lys Val Thr Ile Asp Ile Ser Asn Ser
    130                 135                 140

Phe Arg Asn Ile Ser Ser Lys Cys Asn Glu Leu Arg Glu Lys Tyr Pro
145                 150                 155                 160

Ser Leu Ile Pro Ala Asp Lys Asn Ser Pro Pro Asn Ile Thr Phe Lys
                165                 170                 175

Lys Ala Val Gln Leu Tyr Val Lys Asn Phe Ser Thr Cys Asn Val Met
            180                 185                 190

Tyr Ala Lys Lys Leu Leu Arg Leu Val Ala Gln Ser Glu Lys Ile Glu
        195                 200                 205

Ala Glu Val Ser Arg Ala Val Glu Arg Thr Asn Ala Ser Thr Met Glu
    210                 215                 220

Leu Ala Lys Leu Asp Lys Val Ala Val Gln Leu Asn Lys Asp Ile Thr
225                 230                 235                 240

Ser Asn Arg Thr Trp Ala Gly Cys Lys Leu Ala Glu Tyr His Gly Gln
                245                 250                 255

Met Asn Phe Val Phe Met Gly Phe Tyr Val Leu Leu Ser Asp Ile Leu
            260                 265                 270

Asp Glu Leu His Ser Leu Leu Lys Lys Ser Lys Ser Met Gln Pro Thr
        275                 280                 285

Arg Leu Thr Gln Glu Glu Val Arg Arg Ala Leu Ser Lys Ala Glu Gln
    290                 295                 300
```

-continued

Val Cys His Asp Val Ser Arg Phe Val Lys Ser Leu Gly Ser Thr Leu
305 310 315 320

Arg Asp Phe Thr Asn Phe Val His Arg Leu Arg Lys Glu Tyr Leu His
325 330 335

Gly Ile Leu Arg Asn Ala Ser Gly Phe Arg Glu Ser Phe Glu Arg Cys
340 345 350

Tyr Lys Val Ala Thr Asn Asn Ser Val Thr Arg Leu Glu Ser Thr Val
355 360 365

Glu Glu Ile Thr Ala Asn Asn Glu Asn Ile Ala Ala Trp Glu Ser Met
370 375 380

Thr Val His Gln Trp Lys Asp Val Ser Lys Lys Leu Arg Gln Ser Leu
385 390 395 400

Leu Thr Val Leu Gly Gly Ser Asn Glu Tyr Ile Leu Leu Tyr Gly Tyr
405 410 415

Phe Gln Glu Phe Asp Ser Met Ser Val Arg Glu Phe Ser Asn Thr Val
420 425 430

Arg Ala Phe Arg Gln Ser Ile Thr Glu Met Ser Val Ala Arg Asn Val
435 440 445

Val Gly Val Ala Ala Lys Thr Val Ala Ala Asp Arg Lys Arg Ile Leu
450 455 460

Cys Arg Ser Val Leu Met Phe Asn Lys Gly Thr Ala Gly Ser Glu Ser
465 470 475 480

Ala Arg Lys Leu Tyr Glu Leu Cys Lys Thr Arg Met Pro Val Glu Glu
485 490 495

Pro Asp Ser Ser Arg Glu Asp Gly Val Val Gly Thr Ser Gly Ser Glu
500 505 510

Glu Glu Ile Ser Gly Lys Asp Gly Gly Thr Ser Phe Ser Val Ser Asp
515 520 525

Ala Asp Tyr Trp Glu Trp Asp Val Pro Pro Lys Val Leu Glu Glu Ser
530 535 540

Ser Gly Asp Leu Leu Tyr Asp Thr Ala Val Asp Leu His Thr Lys Arg
545 550 555 560

Lys Ser Pro Phe Tyr Gln Val Gly Ser Ile Ala Phe Gly Val Phe Leu
565 570 575

Leu Val Val Ser Cys Gly Val Gly Ile Leu Met Phe Val Arg Arg Trp
580 585 590

Tyr Ala Ala Cys Val Ala Arg Ser Ala Asp Gly Gly Thr Asp Cys
595 600 605

<210> SEQ ID NO 3
<211> LENGTH: 28
<212> TYPE: DNA
<213> ORGANISM: Artificial
<220> FEATURE:
<223> OTHER INFORMATION: Synthetic Primer

<400> SEQUENCE: 3
gcacctaacg ctgcaggtgg accatccg 28

<210> SEQ ID NO 4
<211> LENGTH: 29
<212> TYPE: DNA
<213> ORGANISM: Artificial
<220> FEATURE:
<223> OTHER INFORMATION: Synthetic Primer

<400> SEQUENCE: 4

-continued

```
tggtccacct gcagcgttag gtgctgggc                                   29


<210> SEQ ID NO 5
<211> LENGTH: 31
<212> TYPE: DNA
<213> ORGANISM: Artificial
<220> FEATURE:
<223> OTHER INFORMATION: Synthetic Primer

<400> SEQUENCE: 5

caaagacctc gctgcgccca tcgagagaac c                                31


<210> SEQ ID NO 6
<211> LENGTH: 30
<212> TYPE: DNA
<213> ORGANISM: Artificial
<220> FEATURE:
<223> OTHER INFORMATION: Synthetic Primer

<400> SEQUENCE: 6

gatggcgcag cgaggtcttt gttgttgacc                                  30
```

TRYPANOSOMAL VACCINE

CROSS-REFERENCE TO RELATED APPLICATIONS

This application is a U.S. National Stage Application under 35 U.S.C. § 371 which claims the benefit of priority to International Patent Application No. PCT/GB2020/050023, filed Jan. 7, 2020, which claims the benefit of priority to GB Patent Application No. 1900192.4 filed Jan. 7, 2019, each of which is hereby incorporated by reference in its entirety.

FIELD OF THE INVENTION

The invention relates to a trypanosomal vaccine, to pharmaceutical compositions comprising said vaccine and to their uses in vaccination to prevent trypanosomal infection in a mammal.

BACKGROUND OF THE INVENTION

The livelihoods of millions of people living in Africa are at risk due to infectious diseases that affect the health of livestock animals that provide them with essential food, milk, clothing and draught power. One major livestock disease is animal African trypanosomiasis (AAT) which is caused by blood-dwelling *Trypanosome* parasites that affect many important farm animals including cattle, goats, sheep, horses, and pigs. AAT is endemic from the Southern edge of the Sahara to Zimbabwe/Mozambique and is estimated to cause annual productivity losses of over $1 billion, representing a major barrier for the socioeconomic advancement of many African countries. Such is the impact of this disease that the United Nations Food and Agricultural Organisation consider it to "lie at the heart of Africa's struggle against poverty".

The disease is mainly caused by two species of *Trypanosome: T. congolense* and *T. vivax* which are transmitted through the bite of an infected tsetse fly. *T. vivax* transmission does not require tsetse flies for transmission and can be transmitted by other biting insects; as a consequence, *T. vivax* is a problem in countries outside of Africa, primarily Brazil. The few drugs available for AAT are not satisfactory: they cause serious side effects, and parasite resistance to these drugs is increasing. Importantly, even if new effective drugs were developed, these *Trypanosome* parasites are endemic in wild animals meaning there would be little chance of eradicating the disease, and so livestock animals would require constant monitoring and treatment. The best solution would be the deployment of an effective vaccine; however, vaccinating against *Trypanosome* infections has long been considered unachievable because the surface of these parasites is immunologically protected by a highly abundant cell surface protein called the variable surface glycoprotein (VSG). VSGs comprise a large family of related but not identical proteins, and trypanosomes express a small number or even a single variant on their surface at any one time. Host antibodies to VSG alleles are able to kill parasites; however, individual parasites within a population of trypanosomes can switch between variants and those that have switched to an antigenically distinct variant are able to effectively evade the host immune response ensuring the survival of the population as a whole.

One commonly-used strategy in the development of vaccines is to use inactivated or attenuated parasites, however, these vaccines are difficult to manufacture and can some-times cause outbreaks if not appropriately attenuated. Modern vaccines, therefore, are typically purified recombinant proteins that can elicit protective immune responses and are consequently chemically defined.

There is therefore a great need to provide an alternative and effective vaccine against trypanosomes such as *T. vivax*.

SUMMARY OF THE INVENTION

According to a first aspect of the invention, there is provided a trypanosomal vaccine comprising a protein which comprises the amino acid sequence as set forth in SEQ ID NO: 1, or a protein having at least 90% sequence identity to said amino acid sequence, or a fragment of said amino acid sequence thereof, or a nucleic acid molecule encoding said protein.

According to a further aspect of the invention, there is provided a pharmaceutical composition comprising a trypanosomal vaccine as defined herein.

According to a further aspect of the invention, there is provided a method of preventing trypanosomal infection in a mammal which comprises administering to the mammal a therapeutically effective amount of the vaccine composition as defined herein.

According to a further aspect of the invention, there is provided a method of inducing an immune response in a mammal, wherein the method includes administering to the mammal, an effective amount of the vaccine composition as defined herein.

According to a further aspect of the invention, there is provided a kit of parts comprising a vaccine composition as defined herein, a medical instrument or other means for administering the vaccine composition and instructions for use.

DETAILED DESCRIPTION OF THE INVENTION

According to a first aspect of the invention, there is provided a trypanosomal vaccine comprising a protein which comprises the amino acid sequence as set forth in SEQ ID NO: 1, or a protein having at least 90% sequence identity to said amino acid sequence, or a fragment of said amino acid sequence thereof, or a nucleic acid molecule encoding said protein.

The present invention relates to the identification of non-variant cell surface *T. vivax* proteins, which, when used in the context of a vaccine can elicit protective immune responses. Using the genome sequence to identify potential candidates, a vaccine target antigen has been identified which, when produced as a purified recombinant protein and administered with an appropriate immunostimulatory adjuvant, confers protection to *T. vivax* infections in mice. The results presented herein indicate that this non-variant parasite protein will be an important component of a vaccine to prevent AAT in livestock animals.

References herein to the amino acid sequence set forth in SEQ ID NO: 1 refer to:

```
                                      (SEQ ID NO: 1)
MRCHEPPTPPQLSATCCVAEEIDTYNKHLDALMQIIGDAIKNISTNEDNAR

ARAEGLKGCNLHYVQFAVAHTEGSVVAARREAVKAQNTIKGSTSLLKKVTI

DISNSFRNISSKCNELREKYPSLIPADKNSPPNITFKKAVQLYVKNFSTCN

VMYAKKLLRLVAQSEKIEAEVSRAVERTNASTMELAKLDKVAVQLNKDITS

NRTWAGCKLAEYHGQMNFVFMGFYVLLSDILDELHSLLKKSKSMQPTRLTQ

EEVRRALSKAEQVCHDVSRFVKSLGSTLRDFTNFVHRLRKEYLHGILRNAS

GFRESFERCYKVATNNSVTRLESTVEEITANNENIAAWESMTVHQWKDVSK

KLRQSLLTVLGGSNEYILLYGYFQEFDSMSVREFSNTVRAFRQSITEMSVA

RNVVGVAAKTVAADRKRILCRSVLMFNKGTAGSESARKLYELCKTRMPVEE

PDSSREDGVVGTSGSEEEISGKDGGTSFSVSDADYWEWDVPPKVLEESSGD

LLYDTAVDLHTKRKSPFYQVGS.
```

The amino acid sequence of SEQ ID NO: 1 corresponds to the ectodomain of a cell surface *T. vivax* protein known as TvY486_0807240.

The full length amino acid sequence of TvY486_0807240 is shown below:

(SEQ ID NO: 2)
MEVMLFDYFHVLPISCKPRNFCIAFMLMFLRFCPVFAMRCHEPPTPPQLSA
TCCVAEEIDTYNKHLDALMQIIGDAIKNISTNEDNARARAEGLKGCNLHYV
QFAVAHTEGSVVAARREAVKAQNTIKGSTSLLKKVTIDISNSFRNISSKCN
ELREKYPSLIPADKNSPPNITFKKAVQLYVKNFSTCNVMYAKKLLRLVAQS
EKIEAEVSRAVERTNASTMELAKLDKVAVQLNKDITSNRTWAGCKLAEYHG
QMNFVFMGFYVLLSDILDELHSLLKKSKSMQPTRLTQEEVRRALSKAEQVC
HDVSRFVKSLGSTLRDFTNFVHRLRKEYLHGILRNASGFRESFERCYKVAT
NNSVTRLESTVEEITANNENIAAWESMTVHQWKDVSKKLRQSLLTVLGGSN
EYILLYGYFQEFDSMSVREFSNTVRAFRQSITEMSVARNVVGVAAKTVAAD
RKRILCRSVLMFNKGTAGSESARKLYELCKTRMPVEEPDSSREDGVVGTSG
SEEEISGKDGGTSFSVSDADYWEWDVPPKVLEESSGDLLYDTAVDLHTKRK
SPFYQVGSIAFGVFLLVVSCGVGILMFVRRWYAACVARSADGGTDC wherein the underlined portion represents the ectodomain region of TvY486_0807240.

Figure 4:
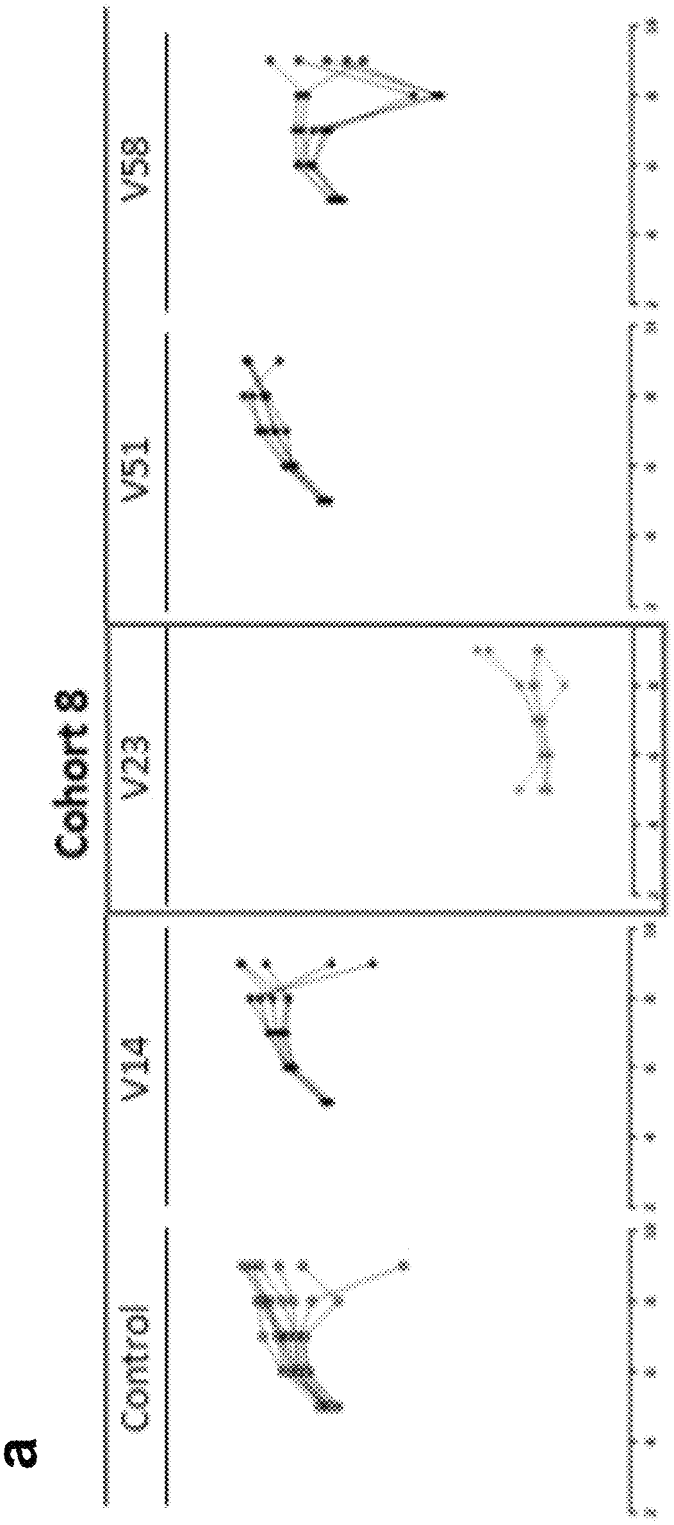
FIG. 4: V23/IFX induces sterile immunity in a *T. vivax* infection model. a, Cohorts of mice vaccinated with the indicated proteins were challenged with luciferase-expressing *T. vivax* parasites and bioluminescence measured on days 5 to 10 following challenge. Adjuvant-only controls are labelled as "Control". V23/IFX elicited sterile protection and is highlighted with a box. y axis is Bioluminescence (ph/s) and x axis is Time post-challenge (days). b, Bioluminescent imaging of adjuvant-only control and mice vaccinated with V23/IFX six and eight days after challenge with *T. vivax*. c, Quantification of repeat bioluminescent *T. vivax* infections in larger cohorts of 15 mice with IFX showing protective effects in the initial screen. Bars indicate mean±SD, ns=not significant, ****P≤0.00001 student t-test.

TvY486_0807240 is also referred to herein as either V23 or IFX (invariant flagellum antigen from *T. vivax*). Data is presented herein which surprisingly shows that IFX elicited complete parasite protection in vaccinated animals in an initial study. In a repeat study, IFX elicited robust protection with all animals showing a marked delay in the establishment of infection and 10 out of the 15 animals were protected (see Study 2 and FIG. 4). This, coupled with the remaining data presented herein from both Study 1 and Study 2, indicate that IFX represents a very attractive candidate for *T. vivax* infection.

In one embodiment, the trypanosomal vaccine as defined herein comprises a protein which comprises the amino acid sequence as set forth in SEQ ID NO: 1, or a protein having at least 90% sequence identity to said amino acid sequence, or a fragment of said amino acid sequence thereof.

It will be appreciated that references herein to "identity" are to be understood as meaning the percentage identity between two protein sequences, e.g.: SEQ ID NO: X and SEQ ID NO: 1, which is the sum of the common amino acids between aligned sequences SEQ ID NO: X and SEQ ID NO: 1, divided by the shorter length of either SEQ ID NO: X or SEQ ID NO: 1, expressed as a percentage.

In one embodiment, the protein of the invention has greater than 90% sequence identity with the ectodomain region of TvY486_0807240 (SEQ ID NO: 1), such as at least 91%, 92%, 93%, 94%, 95%, 96%, 97%, 98% or 99% sequence identity with the ectodomain region of TvY486_0807240 (SEQ ID NO: 1).

References herein to 'fragment' include, for example, functional fragments with a C-terminal truncation, or with an N-terminal truncation. Fragments are suitably greater than 10 amino acids in length, for example greater than 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 amino acids in length.

In a further embodiment, the protein of the invention consists of the amino acid sequence as set forth in SEQ ID NO: 1.

In an alternative embodiment, the vaccine comprises a nucleic acid molecule encoding said protein of the invention. References herein to "nucleic acid molecule" typically refers to DNA or RNA. In a further embodiment, the nucleic acid molecule comprises an oligonucleotide encoding said protein.

References herein to "trypanosomal" refer to a genus of kinetoplastids (class Kinetoplastida), a monophyletic group of unicellular parasitic flagellate protozoa. The name is derived from the Greek trypano- (borer) and soma (body) because of their corkscrew-like motion. Most trypanosomes are heteroxenous (requiring more than one obligatory host to complete life cycle) and most are transmitted via a vector. The majority of species are transmitted by blood-feeding invertebrates, but there are different mechanisms among the varying species. Some, such as *Trypanosoma equiperdum*, are spread by direct contact. In an invertebrate host they are generally found in the intestine, but normally occupy the bloodstream or an intracellular environment in the mammalian host.

Examples of trypanosomal species include: *T. ambystomae, T. antiquus, T. avium, T. boissoni, T. brucei, T. cruzi, T. congolense, T. equinum, T. equiperdum, T. evansi, T. everetti, T. hosei, T. irwini, T. lewisi, T. melophagium, T. paddae, T. parroti, T. percae, T. rangeli, T. rotatorium, T. rugosae, T. sergenti, T. simiae, T. sinipercae, T. suis, T. theileri, T. triglae, T. tungarae* and *T. vivax.*

In one embodiment, the trypanosomal vaccine is a *T. congolense* or *T. vivax* vaccine. In a further embodiment, the trypanosomal vaccine is a *T. vivax* vaccine.

According to a further aspect of the invention, there is provided a pharmaceutical composition comprising a trypanosomal vaccine as defined herein.

In one embodiment, the vaccine composition additionally comprises one or more adjuvants. References herein to the term "adjuvant" refer to a compound that, when used in combination with a specific immunogen in a formulation, will augment or otherwise alter or modify the resultant immune response. Modification of the immune response can include intensification or broadening the specificity of either or both antibody and cellular immune responses. Modification of the immune response can also mean decreasing or suppressing certain antigen-specific immune responses.

In one embodiment, at least about 1 ng and up to about 50 ng adjuvant is present within the vaccine composition. In a further embodiment, at least about 1 μg and up to about 20 μg adjuvant is present within the vaccine composition. Examples of suitable adjuvants include: alum; aluminum hydroxide; aluminum phosphate; calcium phosphate hydroxide; paraffin oil; killed bacteria such as *Bordetella pertussis, Mycobacterium bovis* and toxoids; squalene, detergents; plant saponins from quillaja, soybean, polygala senega; cytokines such as IL-1, IL-2, IL-12; Freund's complete adjuvant; and Freund's incomplete adjuvant. One further example of a suitable adjuvant includes TiterMax® Gold Adjuvant (Sigma-Aldrich) which contains three essential ingredients: a block copolymer, CRL-8300, squalene (a metabolizable oil) and a sorbitan monooleate.

In a yet further embodiment, said adjuvant comprises aluminium hydroxide, such as a wet gel suspension of aluminium hydroxide, in particular Alhydrogel®, more particularly Alhydrogel® 2%. In one particular embodiment, said adjuvant comprises Montanide® ISA 201 VG. This adjuvant is a water-in-oil-in-water adjuvant and full details of this adjuvant may be found: https://www.seppic.com/montanide-isa-w-o-w. In an alternative embodiment, said adjuvant comprises Quil-A®. Quil-A® adjuvant is a saponin adjuvant which is used in a wide variety of veterinary vaccines. Full details of Quil-A® may be found: https://www.invivogen.com/quila. Data is presented herein which demonstrates that this adjuvant was just as effective as aluminium hydroxide (alum) alone in eliciting immune responses (see Study 2 and FIG. 8*a*).

In one embodiment, the vaccine composition additionally comprises a pharmaceutically acceptable carrier, diluent, excipient, or combination thereof, in which the immunogen (i.e. the proteins as defined herein) is/are suspended or dissolved.

Pharmaceutically acceptable carriers are known, and include but are not limited to, water for injection, saline solution, buffered saline, dextrose, water, glycerol, sterile isotonic aqueous buffer, and combinations thereof. For parenteral administration, such as subcutaneous injection, the carrier may include water, saline, alcohol, a fat, a wax, a buffer or combinations thereof. Pharmaceutically acceptable carriers, diluents, and other excipients are described in detail in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

In other embodiments, the vaccine composition can include one or more diluents, preservatives, solubilizers and/or emulsifiers. For example, the vaccine composition can include minor amounts of wetting or emulsifying agents, or pH buffering agents to improve vaccine efficacy. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

It may also be desirable to include other components in a vaccine composition, such as delivery vehicles including but not limited to aluminum salts, water-in-oil emulsions, biodegradable oil vehicles, oil-in-water emulsions, biodegradable microcapsules, and liposomes. In other embodiments, the vaccine composition can include antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Administration of the vaccine composition can be systemic or local. Methods of administering a vaccine composition include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions described herein are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition may induce an antibody or other immune response that is substantially higher than other routes of administration. In another embodiment, intranasal or other mucosal routes of administration of a composition described herein may induce an antibody or other immune response at the site of immunization.

In one embodiment, the vaccine composition has a volume of between about 50 µl and about 10 ml, such as 1 ml.

According to a further aspect of the invention, there is provided a method of preventing trypanosomal infection in a mammal which comprises administering to the mammal a therapeutically effective amount of the vaccine composition as defined herein.

References herein to "trypanosomal infection" refer to infection by a *Trypanosome* as defined herein, such as *T. congolense* or *T. vivax*, in particular *T. vivax*. Thus, in one embodiment, the trypanosomal infection is an infection mediated by *Trypanosoma vivax*.

In one embodiment, the trypanosomal infection is animal African trypanosomiasis (AAT).

References herein to "effective amount" refer to a dose which is sufficient or most likely to elicit antibodies such that the immunized subject has reduced severity of infection.

According to a further aspect of the invention, there is provided a method of inducing an immune response in a mammal, wherein the method includes administering to the mammal, an effective amount of the vaccine composition as defined herein.

Examples of suitable mammals include ungulates, such as those selected from cattle, goats, sheep, horses, pigs and camels.

In one embodiment, the vaccine composition is administered in a single dose regimen. In another embodiment, the vaccine composition is administered in a two dose regimen that includes a first and a second dose. In one embodiment, the second dose is administered at least about 1 week, 2 weeks, 3 weeks, 1 month or 1 year after the first dose. In another embodiment, the vaccine composition is administered in a three dose regimen.

According to a further aspect of the invention, there is provided a kit of parts comprising a vaccine composition as defined herein, a medical instrument or other means for administering the vaccine composition and instructions for use.

In one embodiment, the vaccine composition is packaged in a hermetically sealed container such as an ampoule or sachette indicating the quantity of composition. In one embodiment, the composition is supplied as a liquid. In another embodiment, the composition is supplied as a dry sterilized lyophilized powder or water free concentrate in a hermetically sealed container, wherein the composition can be reconstituted, for example, with water or saline, to obtain an appropriate concentration for administration to a subject.

When the vaccine composition is systemically administered, for example, by subcutaneous or intramuscular injection, a needle and syringe, or a needle-less injection device can be used. The vaccine formulation can be enclosed in ampoules, disposable syringes or multiple dose vials made of glass or plastic.

The following studies illustrate the invention:

Study 1

Materials And Methods

Design, synthesis and purification of *T. vivax* TvY486_0807240 The region corresponding to the entire extracellular domains of TvY486_0807240 was determined by using transmembrane (TMHMMv2.0 (Sonnhammer et al. (1998) Proceedings International Conference on Intelligent Systems for Molecular Biology 6, 175-182) and signal peptide prediction software (SignalP v4.0 (Petersen et al. (2011) Nature methods 8, 785-786)). Sequences encoding the entire extracellular domains of these proteins from the Y486 strain of *Trypanosoma vivax*, with the exception of their signal peptide, were made by gene synthesis (GeneartAG, Germany and Twist Bioscience, USA). All sequences were codon-optimized for expression in human cells. The coding sequences were flanked by unique Notl and Ascl sites and cloned into a derivative of the pTT3 expression vector between the leader sequence of the mouse variable light chain 7-33 (Crosnier et al. (2013) Molecular & cellular proteomics: MCP≤12, 3976-3986). The ectodomain was expressed as a soluble recombinant protein in HEK293 cells as described (Crosnier et al. (2013), supra). Protein was purified by Ni2+ immobilised metal ion affinity chromatography using HisTRAP columns (GEHealthcare, UK), eluted in 400 mM imidazole as described (Bartholdson et al. (2012) PLoS pathogens 8, e1003031), dialysed into HBS, aliquoted and snap-frozen prior to immunisation.

Animals, Immunisations, Challenge and Bioluminescence Measurement

All animal experiments were performed in accordance with UK Home office legislation and according to local ethical review board approval. Six to eight-week old female BALB/c mice were bred and housed at the Research Support Facility of the Wellcome Trust Sanger Institute. Recombinant proteins were adsorbed to Alhydrogel® adjuvant 2% (Brenntag Biosector, Denmark) as an adjuvant using a final volume ratio of 1:1. Animals were immunised intraperitoneally with an initial priming dose of 80 micrograms followed by two further booster immunisations of 80 and 50 micrograms given at two week intervals.

Vaccinated animals were rested for 4 weeks after the final immunisation to mitigate any possible non-specific protective effects elicited by residual adjuvant. Animal challenges were performed using a transgenic form of the *T. vivax* Y486 strain genetically engineered to ubiquitously express the firefly luciferase enzyme as described (Chamond et al. (2010) PLoS neglected tropical diseases 4, e792). Parasites were maintained by weekly passage in wild type BALB/c mice. For infection challenges, bloodstream forms of *T. vivax* parasites were obtained from the blood of an infected donor mouse at the peak of parasitaemia and between 100 to 1000 parasites were used to infect mice by intravenous injection.

From day three post-infection, animals were injected intraperitoneally with luciferase substrate, D-luciferin (D-Luciferin potassium salt, Source BioScience, Nottingham, UK) at a dose of 200 mg/kg, 10 mins before bioluminescence acquisitions. The mice were anaesthetized with 3% isoflurane and placed in the imaging chamber for analysis. Emitted photons were acquired by a charge coupled device (CCD) camera (IVIS Spectrum Imaging System, Perkin Elmer). Total photons emitted from the image of each mouse were quantified using Living Image software (Xenogen Corporation, Almeda, California), and results were expressed as number of photons/sec/ROI. Seven days post-challenge, thin-film parasitemia quantification was conducted where blood parasite counts were established under a light microscope and expressed as the number of parasites per millilitre of blood as an independent measurement of parasite load.

Results

To discover potential subunit vaccine candidates for *T. vivax*, we analysed the genome sequence to identify proteins that fulfilled the following criteria: 1) were predicted to encode cell surface proteins that would be accessible to vaccine-elicited host antibodies; 2) did not belong to a paralogous group of parasite proteins that might indicate functional redundancy; 3) contained more than 300 amino acids and so are likely to project beyond the VSG coat on the parasite membrane. A protein that met these criteria was TvY486_0807240.

To increase the chances that the extracellular regions of the protein were expressed in a correctly folded conformation and therefore elicit antibodies that would bind to the native parasite protein, we expressed the protein using a mammalian expression system to promote the formation of structurally-critical disulphide bonds. The entire ectodomain region was identified and the gene constructed by gene synthesis using codons optimised for expression in human cells. This gene construct was cloned into a mammalian protein expression plasmid.

Figure 1:
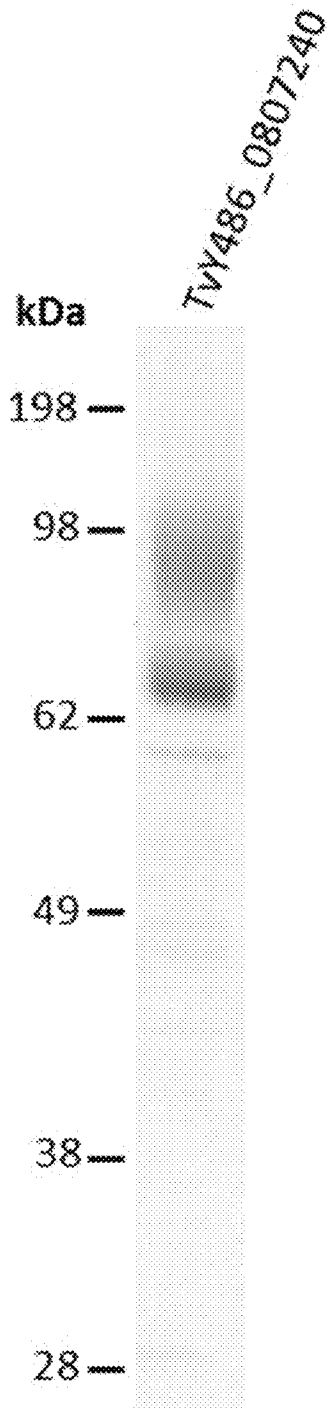
FIG. 1: Expression and purification of the extracellular regions of TvY486_0807240. Protein consisting of the entire ectodomain was expressed as a soluble recombinant protein in HEK293 cells and purified from spent tissue culture media using immobilised metal ion chromatography. Approximately one microgram of purified protein was resolved by SDS-PAGE under reducing conditions. The protein migrated as a series of glycoforms around the expected mass.

Human embryonic kidney (HEK)293 cells were transfected with this plasmid and the protein secreted into the tissue culture medium. The protein was purified from the tissue culture supernatant by immobilised metal ion chromatography (IMAC) and resolved as a series of glycoforms by SDS-PAGE (FIG. 1).

Figure 2:
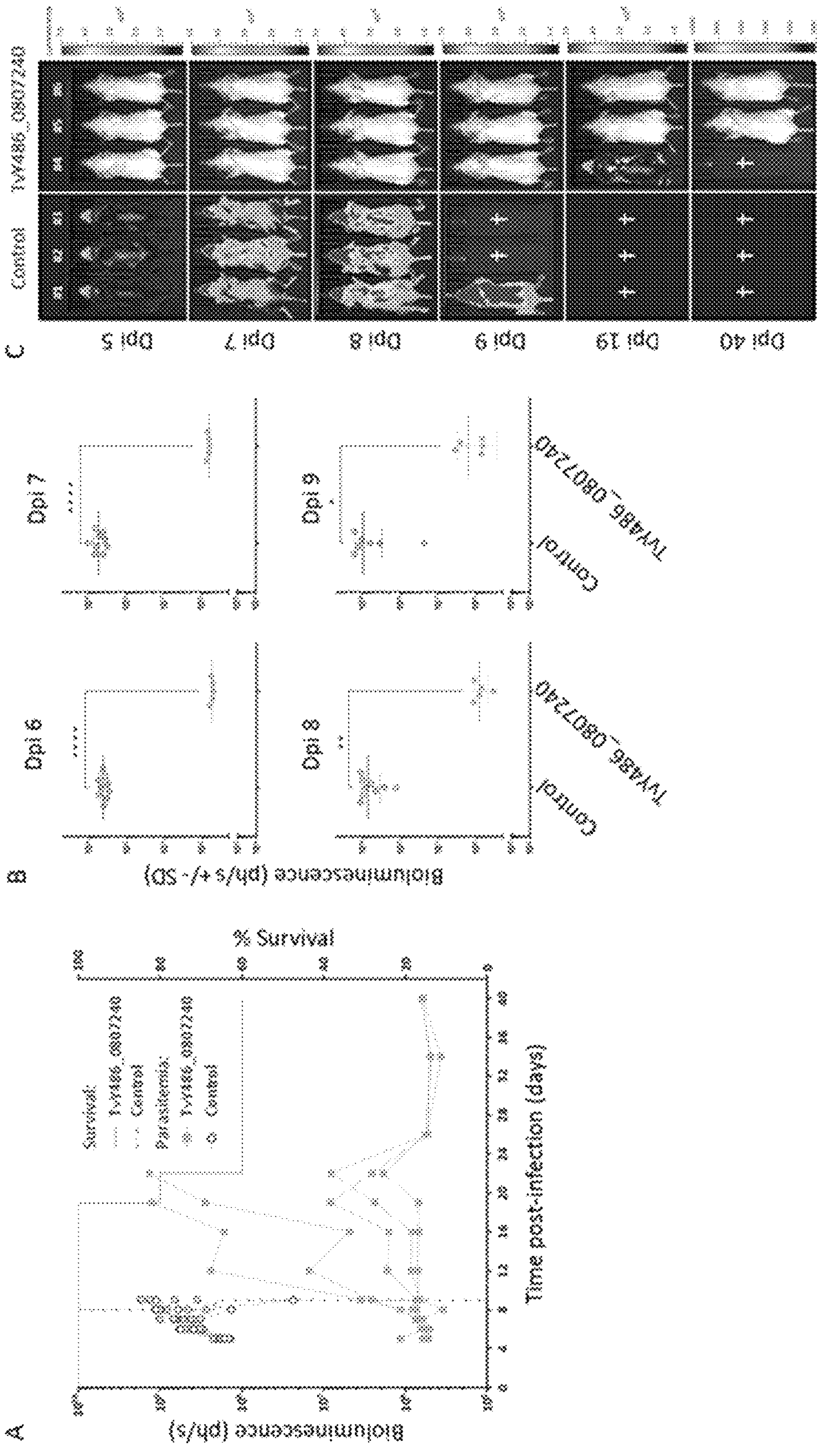
FIG. 2: Vaccination with the ectodomains of TvY486_0807240 confer protection in a murine model of *T. vivax* infection. (A) Five animals were vaccinated with TvY486_0807240 (solid line, filled squares) show attenuated *T. vivax* parasitaemia relative to adjuvant-only control animals (dotted lines, open circles). Parasitaemia was quantified in each animal by bioluminescence using the firefly luciferase gene transgenically expressed by the *T. vivax* strain used and plotted as a function of time post-infection. Survival curves indicate when animals were withdrawn from the study. (B) Comparisons of the parasitaemia on the indicated days post-infection in the vaccinated and control animals. Data points represent individual animals and horizontal bar represents mean±s.d. Comparisons were made using a one-way ANOVA with Dunnett's multiple comparison test for statistical confidence where * P≤0.01; P≤0.001; **P≤0.00001. (C) Exemplar bioluminescence images of three control animals (numbers 1 to 3) and three vaccinated (numbers 4 to 6) on the indicated days post-infection. A cross indicates that the animal was removed from the study.
Figure 3:
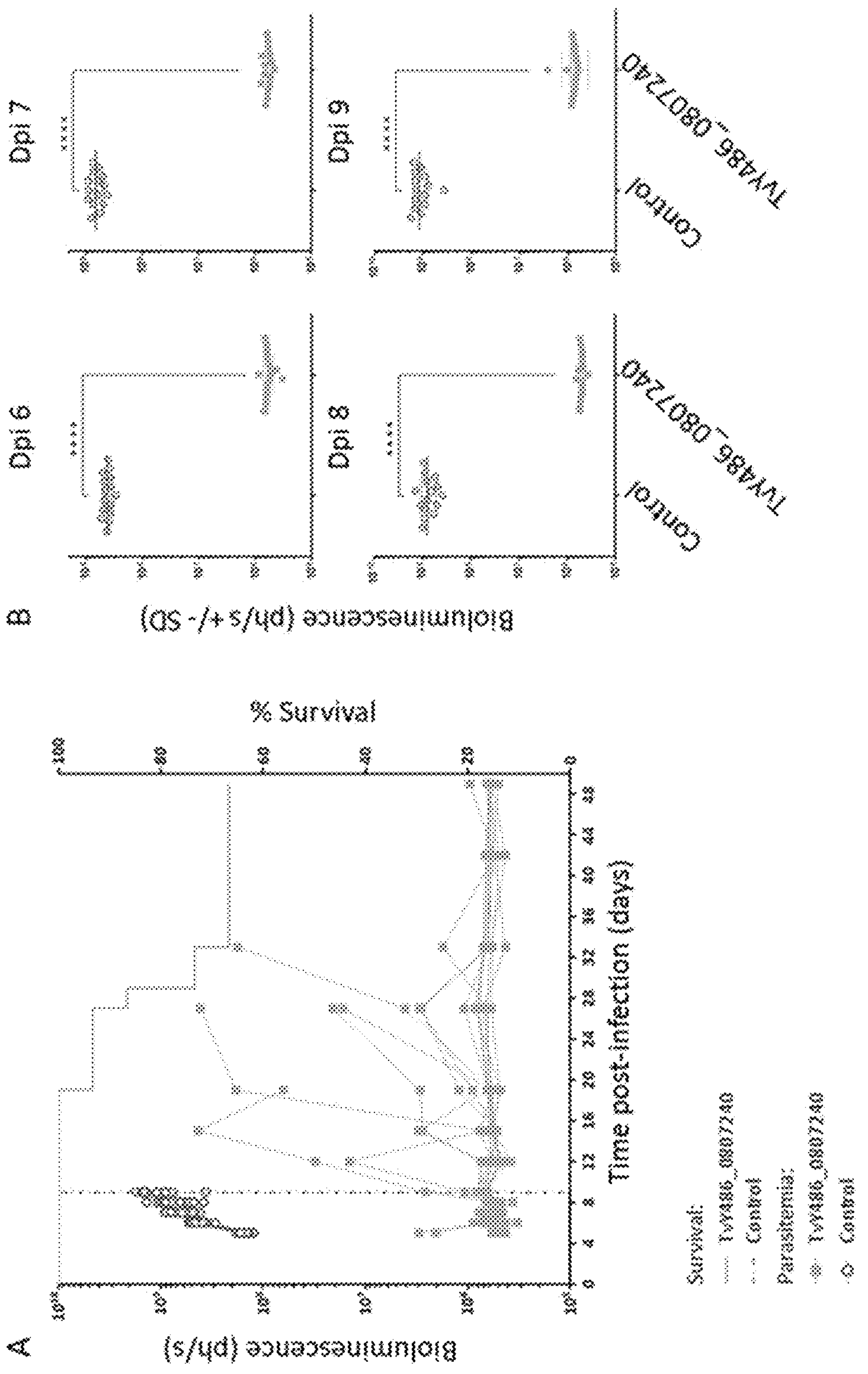
FIG. 3: Repeat vaccinations with an independent preparation of TvY486_0807240 in a larger cohort conforms vaccine effect in a murine model of *T. vivax* infection. (A) Fifteen animals were vaccinated with TvY486_0807240 (solid line filled squares) show attenuated *T. vivax* parasitaemia relative to adjuvant-only control animals (dotted lines open circles). Parasitaemia was quantified in each animal by bioluminescence using the firefly luciferase gene transgenically expressed by the *T. vivax* strain used and plotted as a function of time post-infection. Survival curves indicate when animals were withdrawn from the study. (B) Comparisons of the parasitaemia on the indicated days post-infection in the vaccinated and control animals. Data points represent individual animals and horizontal bear represents mean±s.d. Comparisons were made using the student t-test where statistical confidence is indicated as ****P≤0.00001.

Groups of five mice were immunised intraperitoneally using a prime followed by two boost regime with the protein adjuvanted with Alhydrogel; control animals were immunised with adjuvant only. Vaccinated animals were challenged with *T. vivax* parasites delivered intravenously from the blood of an infected donor animal. Animals immunised with TvY486_0807240 were protected from infection relative to adjuvant-only control mice over the first nine days of infection (FIGS. 2A, 2B and 2C). Three of the five mice immunised with the ectodomain of TvY486_0807240 survived the infection challenge and showed no evidence of parasites by day 40 post-infection. To confirm these results, a larger cohort of 15 animals were immunised with an independent preparation of the TvY486_0807240 ectodomain and again all vaccinated animals were protected up to day 9, a time at which all adjuvant-only controls were removed from the study (FIGS. 3A and 3B). Ten of the fifteen vaccinated animals showed no evidence of parasitaemia at 50 days post infection (FIG. 3A).

Discussion

Animal African trypanosomiasis continues to be a significant impediment in the successful raising of livestock animals in sub-Saharan Africa and previous attempts to vaccinate against the *Trypanosome* parasites that cause this disease have been unsuccessful. Here we have shown that vaccinating with a recombinant protein comprising the entire ectodomain of a conserved *T. vivax* cell surface protein TvY486_0807240 confers protection in a mouse model of infection suggesting that this protein could be an effective subunit vaccine. We note that the disease is acute in the BALB/c mice used in our infection trials since control mice develop rapid uncontrolled parasitaemia whereas in livestock animals such as goats and cattle the infection is typically a chronic disease with lower parasitaemia suggesting the mouse infection model provides a stringent test of our vaccine candidates. We envisage that a vaccine containing TvY486_0807240 in whole or in part and in the context of an appropriate adjuvant will constitute a vaccine to treat this disease in livestock animals.

Study 2

Materials and Methods

Mouse Strains and Ethical Approvals

All animal experiments were performed under UK Home Office governmental regulations (project license number PD3DA8D1F) and European directive 2010/63/EU. Research was ethically approved by the Sanger Institute Animal Welfare and Ethical Review Board. Mice were obtained from the Research Support Facility, Wellcome Sanger Institute.

*Trypanosoma vivax* Parasite Strain and Maintenance

A transgenic form of *Trypanosoma vivax* genetically engineered to ubiquitously express the firefly luciferase enzyme was kindly provided by the Institut Pasteur, Paris. The parental strain of this parasite is the IL1392 line derived from the Y486 strain used for genome sequencing (Jackson et al. 2012, Proc. Natl. Acad. Sci. U.S.A 109, 3416-3421) and is fully documented by Chamond et al. (Chamond et al. 2010, PLoS Negl. Trop. Dis. 4, e792). Parasites were initially recovered from a frozen sample by intraperitoneal administration into two mice and transferred to naïve mice when parasites became patent in the blood. Parasites were maintained by weekly serial blood passage in wild type female BALB/C mice by taking a blood biopsy, quantifying living parasites in PBS/10 mM D-glucose by microscopy and infecting four naive mice by intravenous infection. During the course of the project, two further aliquots of frozen parasites were thawed and then used for infection challenges, no significant differences in the kinetics of infection between the batches of parasites were observed.

Quantification of *Trypanosoma vivax* Infections by Bioluminescent In Vivo Imaging To quantify *T. vivax* infections by bioluminescent in vivo imaging, infected animals were intraperitoneally administered with the luciferase substrate, luciferin. D-luciferin (potassium salt, Source BioScience, UK) was reconstituted to 30 mg $mL^{-1}$ in Dulbecco's PBS without $Ca^{2+}$ and $Mg^{2+}$ (Hyclone), filter-sterilised (0.22 μm) and stored in aliquots at −20° C. Aliquots were thawed and administered to animals at a dose of 200 mg/kg, by intraperitoneal injection ten minutes before bioluminescence acquisitions. The mice were given three minutes of free movement before being anaesthetized with 3% isoflurane and placed in the imaging chamber where anaesthesia was maintained for acquisition. To determine the long-term persistence of the parasites in different organs of infected mice, animals were administered with luciferin, imaged, and then euthanised with an overdose of anaesthetic. Mice were then perfused with PBS until the perfusion fluid ran clear, the organs dissected, arranged on a petri dish, and bathed in PBS containing 10 mM glucose and luciferin for imaging. Emitted photons were acquired by a charge coupled device (CCD) camera (IVIS Spectrum Imaging System, Perkin Elmer). Total photons emitted from the image of each mouse were quantified using Living Image software (Xenogen Corporation, Almeda, California), and the results were expressed as bioluminescence: number of photons/sec/ROI.

Vaccine Target Identification and Expression

The *T. vivax* genome was searched for proteins encoding predicted typel, GPI-anchored and secreted proteins using protein feature searching in TryTrypDB (Aslett et al. 2010, Nucleic Acids Res. 38, D457-D462). The regions corresponding to the entire extracellular domains of *T. vivax* cell-surface and secreted proteins from the Y486 strain were determined by using transmembrane (Sonnhammer et al. 1998, Proc. Int. Conf. Intell. Syst. Mol. Biol. 6, 175-182) and GPI-anchor (Eisenhaber et al. 1999, J. Mol. Biol. 292, 741-758) or signal peptide (Bendtsen et al. 2004, J. Mol. Biol. 340, 783-795) prediction software. Protein sequences encoding the extracellular domain and lacking their signal peptide, were codon-optimized for expression in human cells and made by gene synthesis (GeneartAG, Germany and Twist Bioscience, USA). The sequences were flanked by unique Notl and Ascl restriction enzyme sites and cloned into a pTT3-based mammalian expression vector (Durocher et al. 2002, Nucleic Acids Res. 30, E9) between an N-terminal signal peptide to direct protein secretion and a C-terminal tag that included a protein sequence that could be enzymatically biotinylated by the BirA protein-biotin ligase (Bushell et al. 2008, Genome Res. 18, 622-630) and a 6-his tag for purification (Sun et al. 2012, Anal. Biochem. 424, 45-53). The ectodomain was expressed as a soluble recombinant protein in HEK293 cells which were obtained from Yves Durocher (NRC, Montreal) as described (Crosnier et al. 2013, Mol. Cell. Proteomics 12, 3976-3986; Kerr and Wright 2012, J. Vis. Exp. e3881). Cell lines were regularly tested (every six months, Surrey Diagnostics, UK) for *mycoplasma* contamination and found to be negative. To prepare purified proteins for immunisation, between 50 and 1.2 L (depending on the level at which the protein was expressed) of spent culture media containing the secreted ectodomain was harvested from transfected cells, filtered and purified by $Ni^{2+}$ immobilised metal ion affinity chromatography using HisTRAP columns using an AKTAPure instrument (GEHealthcare, UK). Proteins were eluted in 400 mM imidazole as described (Bartholdson et al. 2012, PLoS Pathog. 8, e1003031), and extensively dialysed into HBS before quantified by spectrophotometry at 280 nm. Protein purity was determined by resolving approximately one microgram of purified protein by SDS-PAGE using NuPAGE 4-12% Bis Tris precast gels (ThermoFisher) for 50 minutes at 200V. Where reducing conditions were required NuPAGE reducing agent and anti-oxidant (Invitrogen) were added to the sample and the running buffer, respectively. The gels were stained with SYPRO Orange (ThermoFisher), destained in 7.5% acetic acid and imaged using a Typhoon 9400 phosphoimager (GE Healthcare). Purified proteins were aliquoted and stored frozen at −20° C. until use. Where enzymatically monobiotinylated proteins were required to determine antibody titres by ELISA, proteins were co-transfected with a secreted version of the protein biotin ligase (BirA) as described (Kerr and Wright 2012, supra), and extensively dialysed against HEPES-buffered saline and their level of expression determined by ELISA.

Vaccine Formulation and Administration

For the initial screening of antigens, aliquots of purified protein for immunisation were thawed, diluted in PBS and mixed 50% v/v with Alhydrogel adjuvant 2% (InvivoGen) for two hours at room temperature. For each antigen, groups of five six to eight-week old female BALB/C mice were immunised intraperitoneally initially with 100 μg protein followed by two additional fortnightly immunisations using 20 μg protein. Where the quantity of purified antigen was insufficient to achieve these levels, lower doses of proteins were administered.

*Trypanosoma vivax* Vaccine Testing

For infection challenges, bloodstream forms of *T. vivax* parasites were obtained from the blood of an infected donor mouse at the peak of parasitaemia, diluted in PBS/10 mM D-glucose, quantified by microscopy, and between 100 to 1000 parasites were used to infect mice by intravenous injection. While establishing the infection model in our facility, we observed that the *T. vivax* parasite was labile and gradually lost virulence once removed from living mice. To reduce the possibility of any artefactual protective effects being due to the loss of parasite virulence during the challenge procedure, we screened the protective effects of antigens in a cohort design. Each cohort contained six cages of five animals: four cages contained mice immunised with a different query subunit vaccine candidate, and the other two cages contained control mice immunised with adjuvant alone. During the infection procedure, the mice in the control cages were challenged first and last and the data from the cohort only used if the infections in the control mice from the two cages were not statistically different. During the infection procedures, parasites were outside of a living mouse for no more than 30 minutes. Eight to ten days after the final immunisation, blood biopsies were collected from the tail of each animal and clotted for two hours at room temperature. Cells were removed by centrifugation and sera collected, sodium azide added to a final concentration of 2 mM and stored at −20° C. Vaccinated animals were rested for four weeks after the final immunisation to mitigate any possible non-specific protective effects elicited by residual adjuvant.

Mice were normally challenged by intravenous delivery of $10^2$ to $10^3$ parasites for the initial screening and passive transfer protection experiments, but were also challenged intraperitoneally during the establishment of the model and subcutaneously when investigating the duration of protection. For retesting antigens, two groups of 15 animals were each housed in three cages containing five mice. The animals were not randomised between cages and the operator was not blinded to the group condition. Groups were compared using bioluminescence quantification as a proxy for parasitaemia and groups were compared using one-way ANOVA. No readings were excluded from the analysis.

Passive Transfer of Immunity

To obtain sufficient sera for adoptive transfer experiments, 50 six to eight-week-old female BALB/C mice were immunised intraperitoneally three times with 20 μg of purified IFX adjuvanted in alum, with each immunisation separated by two weeks. Nine days after the final immunisation, sera were collected as above, aliquoted, and stored at −20° C. until use. For passive transfer experiments, groups of six to eight-week-old female BALB/C mice were dosed three times with either sera or purified monoclonal antibodies on three consecutive days; three hours after the second dosing, mice were challenged intravenously with $10^2$ T. *vivax* parasites. When using immune serum for passive transfer protection experiments, doses of 100 and 200 μL of sera from either IFX-vaccinated mice or non-immunised control mice were administered. For monoclonal antibodies, the purified antibody was diluted to the required dose in PBS and 200 μL administered intravenously.

In Vivo Cell Depletion

Groups of five mice immunised with 50 μg doses of purified V23/IFX were depleted by intraperitoneal administration of lineage-specific monoclonal antibodies using standard procedures. Briefly, NK cells were depleted by four injections of 500 μg of the PK136 mAb that targets the NK1.1 glycoprotein at days −5, −1, 0 and 2 post-infection. CD4 and CD8 T-lymphocytes were depleted by one intraperitoneal 750 μg injection of the mAbs targeting CD4 (clone GK1.5) or CD8 (clone 2.43) receptors, respectively, the day prior of the infection. The LFT-2 mAb (750 μg) was used as a control. Mice were challenged with $10^2$ *T. vivax* parasites and parasitaemia quantified using bioluminescent imaging as described.

*Trypanosome* Genomic Sequence Analysis

To identify if IFX had any homologues in other *Trypanosome* species, the entire IFX sequence was analysed with Interproscan which showed that it does not contain any known protein domains, other than the predicted N-terminal signal peptide and transmembrane helix. Comparison of the predicted IFX protein sequence with all the other sequenced *Trypanosoma* spp. genomes in TriTrypDB (Aslett et al. 2010, supra) using tBLASTx returned no significant matches; moreover, comparison of a Hidden Markov Model of the IFX protein sequence with all *T. brucei, T. congolense* and *T. cruzi* proteins using HMMER also produced no matches demonstrating IFX is unique to *T. vivax*.

Illumina sequencing reads from 29 isolates were mapped to the *T. vivax* Y486 reference sequence using BWA (Li and Durbin 2009, Bioinformatics 25, 1754-1760) before SNPs were called using the GATK4 analysis toolkit (DePristo et al. 2011, Nat. Genet. 43, 491-498). Indels and variant positions with QD<2.0, FS>60.0, MQ<40.0, MQRankSum<−12.5 or ReadPosRankSum<−8.0 were excluded to produce a final list of 403,190 SNPs. Individuals were classified as missing if allele calls were supported by fewer than 3 reads. Coding SNPs and synonymous/non-synonymous codon alterations were identified by comparison to the reference annotation using a custom Biopython script. p values were calculated on a per site basis using vcftools (Danecek et al. 2011, Bioinformatics 27, 2156-2158).

Electron Microscopy

*T. vivax* parasites were resuspended in 1% paraformaldehyde in PBS for 30 minutes (all steps at room temperature), washed three times in PBS, blocked with PBS/glycine followed by 5% foetal calf serum for 30 minutes and then incubated with a mouse monoclonal antibody to IFX (clone 8E12) for 1 hour. After rinsing, the parasites were incubated with goat anti-mouse IgG preadsorbed to 10 nm gold particles (ab27241 Abcam) for 30 minutes, washed, and fixed in a mixture of 2% paraformaldehyde and 2.5% glutaraldehyde in 0.1M sodium cacodylate buffer for 30 minutes. After washing again, the parasites were post-fixed in 1% osmium tetroxide for 30 minutes, dehydrated in an ethanol series, embedded in epoxy resin and 60 nm ultrathin sections were cut on a Leica UC6 ultramicrotome, contrasted with uranyl acetate and lead citrate and examined on a 120 kV FEI Spirit Biotwin using a Tietz F4.16 CCD camera.

Antibody Titre and Isotyping Using ELISA

To determine the antibody titre against an antigen of interest, individual sera were initially diluted 1:2000 and then six four-fold serial dilutions in HBST/2% BSA were prepared. These dilutions were pre-incubated overnight at room temperature with 100 μg/mL of purified rat Cd4d3+4-BLH protein to absorb any anti-biotin/his tag antibodies. Sera were transferred to streptavidin-coated ELISA plates on which the biotinylated target antigen was immobilised. To ensure that all anti-tag antibodies were adsorbed, binding of the lowest dilution of antisera was also tested against biotinylated rat Cd4d3+4-BLH protein similarly immobilised on the ELISA plate to confirm the absence of any anti-tag immunoreactivity. Sera were incubated for one hour at room temperature followed by three washes with HBST before incubating with an anti-mouse IgG secondary antibody conjugated to alkaline phosphatase (Sigma) for one hour. Following three further washes with HBST, 100 μL of 1 mg/mL Sigma 104 phosphatase substrate was added and substrate hydrolysis quantified at 405 nm using a plate reader (Tecan). For ELISA involving cattle sera, sera were diluted 1:500 and an anti-bovine secondary antibody used to quantify immunoreactivity. Sera were obtained from individual natively-infected animals from both Cameroon and Kenya.

Monoclonal Antibody Selection and Characterisation

Hybridomas secreting monoclonal antibodies to IFX were selected using standard protocols as described (Crosnier et al. 2010, BMC Biol. 8, 76). In brief, the SP2/0 myeloma cell line was grown in advanced DMEM/F12 medium (Invitrogen, CA, USA) supplemented with 20% fetal bovine serum, penicillin (100 U/mL), streptomycin (100 μg/mL) and L-glutamine (2 mM). Following spleen dissection and dissociation, $10^8$ splenocytes were fused to $10^7$ SP2/0 myeloma in 50% PEG (PEG 1500, Roche, Hertfordshire, UK), using standard procedures. The resulting hybridomas were plated over ten 96-well plates and initially grown in advanced DMEM/F12 medium (Invitrogen) supplemented with 20% fetal bovine serum, penicillin (100 U/mL), streptomycin (100 μg/mL) and L-glutamine (2 mM) before addition of hypoxanthine-aminopterin-thymidine (HAT) selection medium 24 hours after the fusion. After 11 days, hybridoma supernatants were harvested to determine the presence of antibodies reacting to the IFX protein using an ELISA-based method as previously described (Crosnier et al. 2010, supra). Six wells (2H3, 3D12, 6B3, 8C9, 8E12, and 8F10) containing hybridoma colonies secreting antibodies that reacted with IFX but not a control protein containing the same purification tags were identified and cultured for a further four days in HAT-selection medium. Hybridoma cells from each of the positive wells were cloned by limiting dilution over two 96-well plates at a density of 0.5 cells per well and grown in HAT-free SP2/0 conditioned medium. Eleven days later, twelve wells corresponding to each of the seven clones were selected and tested again by ELISA for reactivity to the IFX protein; three positive wells per clone were chosen for a second round of dilution cloning in the conditions described above. After a final test for reactivity to IFX, a single well from each of the seven positive clones was expanded and adapted to grow in Hybridoma-SFM serum-free medium (Thermo Fisher). Isotyping of the monoclonal antibodies was performed using the Mouse Monoclonal Antibody Isotyping Kit (Sigma-Aldrich), according to the manufacturer's instructions. Briefly, the biotinylated ectodomain of the IFX protein was immobilised on a streptavidin-coated plate, incubated in the presence of the seven different anti-IFX monoclonal antibodies, washed in PBST before adding isotype-specific goat anti-mouse secondary antibodies. Binding was quantified with an alkaline-phosphatase-conjugated anti-goat tertiary antibody followed by a colourimetric phosphatase substrate, and hydrolysis products quantified by absorbance readings at 405 nm.

To determine the location of the anti-IFX monoclonal antibody epitopes, subfragments of the IFX ectodomain corresponding to the boundaries of predicted secondary structure (M1-T251, M1-S472, S135-T251 and N442-S535) were designed, produced by gene synthesis and cloned into a mammalian expression plasmid with an enzymatically biotinylated C-terminal tag (Twist Biosciences, USA). Biotinylated proteins were expressed as secreted recombinant proteins in HEK293 cells as described above and dialysed to remove free D-biotin. Biotinylated IFX fragments were immobilised on a streptavidin-coated plate and binding of the seven mouse monoclonal antibodies was tested by ELISA and detected with an alkaline-phosphatase-conjugated anti-mouse secondary antibody (Sigma-Aldrich) as previously described (Crosnier et al. 2010. supra). Binding of a rabbit polyclonal antibody raised to the entire ectodomains of IFX (Cambridge Research Biochemicals) was used as a positive control for each of the subdomains, and detected with an alkaline-phosphatase-conjugated anti-rabbit secondary antibody (Jackson Immunoresearch).

For affinity-purification of monoclonal antibodies from hybridoma culture supernatants, spent supernatants were supplemented with 0.1M sodium acetate, pH 5.0 immediately before purification on a HiTrap Protein G HP 1 mL column (GE Healthcare) using an AKTA pure instrument. Elution was performed in 0.1M glycine, pH 2.7 followed by immediate neutralisation with 1M Tris-HCl, pH 9.0. Purified antibodies were extensively dialysed against PBS and stored at 4° C. until use. 300 μg purified monoclonal antibodies were chemically biotinylated using a 20-fold molar excess of sulfo-NHS-biotin (ThermoFisher) for two hours at room temperature; to remove excess biotin the solutions were dialysed against 5 L PBS for 16 hours.

Antibody Affinity by Surface Plasmon Resonance

Antibody affinities were determined by SPR essentially as described (Zenonos et al. 2015, J. Exp. Med. 212, 1145-1151) using a Biacore 8K instrument (GE Healthcare, Chicago, IL). To measure antibody interaction affinity rather than avidity, between 400 to 600 RU of biotinylated anti-IFX monoclonal antibodies were immobilised on a streptavidin-coated sensor chip prepared using the Biotin CAPture kit (GE Healthcare); a biotinylated mouse monoclonal antibody (OX68) was used as a non-binding control in the reference flow cell. The entire ectodomain of IFX was used as the analyte which was first purified and resolved by size exclusion chromatography on a Superdex 200 Increase 10/300 column (GE Healthcare, Chicago, IL) in HBS-EP just prior to use in SPR experiments to remove any protein aggregates that might influence kinetic measurements. Increasing concentrations of five two-fold dilutions of 200 nM soluble IFX analyte were injected at 30 μL/min for a contact time of 120 s and dissociation of 600 s. Both kinetic and equilibrium binding data were analyzed in the manufacturer's Biacore 8K evaluation software version 1.1 (GE Healthcare, Chicago, IL). Equilibrium binding measurements were taken once equilibrium had been reached, using reference-subtracted sensorgrams. All experiments were performed at 37° C. in HBS-EP (10 mM HEPES, 150 mM NaCl, 3 mM EDTA, 0.05% v/v P20 surfactant).

Antibody Cloning, Isotype Switching, Mutagenesis, and Purification.

To switch the isotype of the 8E12 anti-IFX monoclonal antibody from IgG1, it was first necessary to amplify the genes encoding the rearranged light and heavy variable regions from the hybridoma; this was performed essentially as described (Crosnier et al. 2010, supra). Briefly, total RNAs were extracted from the cloned 8E12 hybridoma using the RNAqueous-micro total RNA isolation kit (Ambion) followed by reverse transcription with Superscript III (Thermo Fisher). PCR products encoding the rearranged heavy and light chain regions were individually amplified using sets of degenerate oligonucleotides and then assembled in a subsequent fusion PCR using a linker fragment to create a single PCR product containing both the rearranged light and heavy chains, as previously described (Müller-Sienerth et al. 2014, Methods Mol. Biol. 1131, 229-240). The fusion PCR product was ligated using the NotI and AscI restriction sites into an expression plasmid obtained from Addgene (plasmid #114561) in frame with the mouse constant IgG2a heavy chain (Andrews et al. 2019, Elife 8). Competent *E. coli* were transformed and purified plasmids used in small-scale transfections of HEK293 cells to identify those plasmids encoding functional antibodies as described (Staudt et al. 2014, Biochem. Biophys. Res. Commun. 445, 785-790).

To perturb the recruitment of immune effectors in the murine IgG2a recombinant antibody and retain serum half-life, we mutated the C1q and FcR binding sites in the IgG2a constant heavy chain by site-directed mutagenesis as described (Lo et al. 2017, J. Biol. Chem. 292, 3900-3908). Mutation to the binding site of Fcγ receptors (ΔFcR) was achieved by introducing the L234A and L235A substitutions using primers $FcR_f$—5' GCACCTAACGCTGCA GGTGGACCATCCG 3' (SEQ ID NO: 3) and $FcR_f$—5' TGGTCCACCTGCAGCGTTAGGTGCTGGGC 3' (SEQ ID NO: 4). To abrogate C1q binding (ΔC1q), a single amino-acid change P329A was introduced using primers $C1q_f$—5' CAAAGACCTCGCTGCGCCCATCGAG AGAACC 3' (SEQ ID NO: 5) and $C1q_r$—5' GATGGC GCAGCGAGGTCTTTGTTGTTGACC 3' (SEQ ID NO: 6). In both cases, antibody mutagenesis was achieved by first amplifying 20 ng of an expression vector containing the mouse constant IgG2a heavy chain with each oligonucleotide separately for nine cycles (denaturation for 45 seconds at 94° C.; annealing for 40 seconds at 58° C.; elongation for 7 minutes and 30 seconds at 72° C.), using the KOD Hot Start DNA polymerase (Merck).

Amplification reactions performed with complementary oligonucleotides were then mixed, 0.5 μL KOD Hot Start DNA polymerase was added to the reaction, and the amplification was resumed for a further 18 cycles. At the end of the reaction, half of the PCR reaction was digested with 20U Dpnl enzyme (New England Biolabs), which specifically cleaves methylated strands from the parental plasmid, for 3 hours at 37° C. before transforming 5 μL into TOP 10 chemically-competent bacteria (Invitrogen). Mutations were confirmed in selected clones by DNA sequencing. To generate a double mutant lacking both the C1q and FcR binding sites (ΔC1qΔFcR), site-directed mutagenesis was performed as described above on an expression plasmid containing the FcR mutation, using the set of oligonucleotides designed for C1q mutagenesis. Both single mutants and the double mutant backbones were doubly digested with Notl and Ascl restriction enzymes and the fusion PCR product encoding the variable regions of the 8E12 recombinant antibody described above cloned into them, plasmids purified and verified by sequencing.

Antibodies were produced by transfecting HEK293 cells with plasmids encoding the recombinant 8E12 IgG2a monoclonal antibody with the wild-type IgG2a heavy chain, single mutants that lacked C1q and FcR binding, and the double mutant. Six days after transfection, the cell culture supernatant was harvested and the recombinant antibodies were purified on a HiTrap Protein G HP 1 mL column, according to the manufacturer's instructions as described (Crosnier et al. 2010, supra).

Results

IFX Induces Sterile Immunity to *T. vivax*

The gene sequence encoding the entire extracellular region of V23/IFX was synthesised and cloned into a mammalian protein expression plasmid containing a secretion peptide and purification tags. IFX was expressed as a soluble recombinant protein in mammalian HEK293 cells to increase the chances that structurally-critical posttranslational modifications were added and therefore elicit host antibodies that recognize native antigens displayed by the parasite. IFX yielded sufficient protein after purification for the vaccination trials. For vaccination, we selected a prime and two boost regime using alum as an adjuvant to bias host responses towards humoral immunity. To reduce any systemic adjuvant-elicited effects on disease progression, vaccinated animals were rested for four weeks following the final boost before parasite challenge. In preliminary experiments, we observed that *T. vivax* lost virulence once removed from donor animals, and so to avoid confounding effects due to loss of parasite viability during the infection procedure, we ensured that infections were comparable in control animals challenged before and after animals vaccinated with the IFX antigen.

We observed that V23/IFX elicited complete protection in all five vaccinated animals (FIG. 4*a, b*). Experiments were repeated using independent protein preparations and larger cohorts of animals. We observed that V23/IFX vaccination elicited robust protection with all animals showing a marked delay in the establishment of the infection and 10 out of the 15 animals were protected (FIG. 4*c*). Dissection of protected animals following infection revealed no obvious extravascular reservoirs of parasites. Based on these findings, we propose to name the V23 candidate (Tv486_080724) IFX for "invariant flagellum antigen from *T. vivax*".

IFX Localises to the Flagellum

Figure 5:
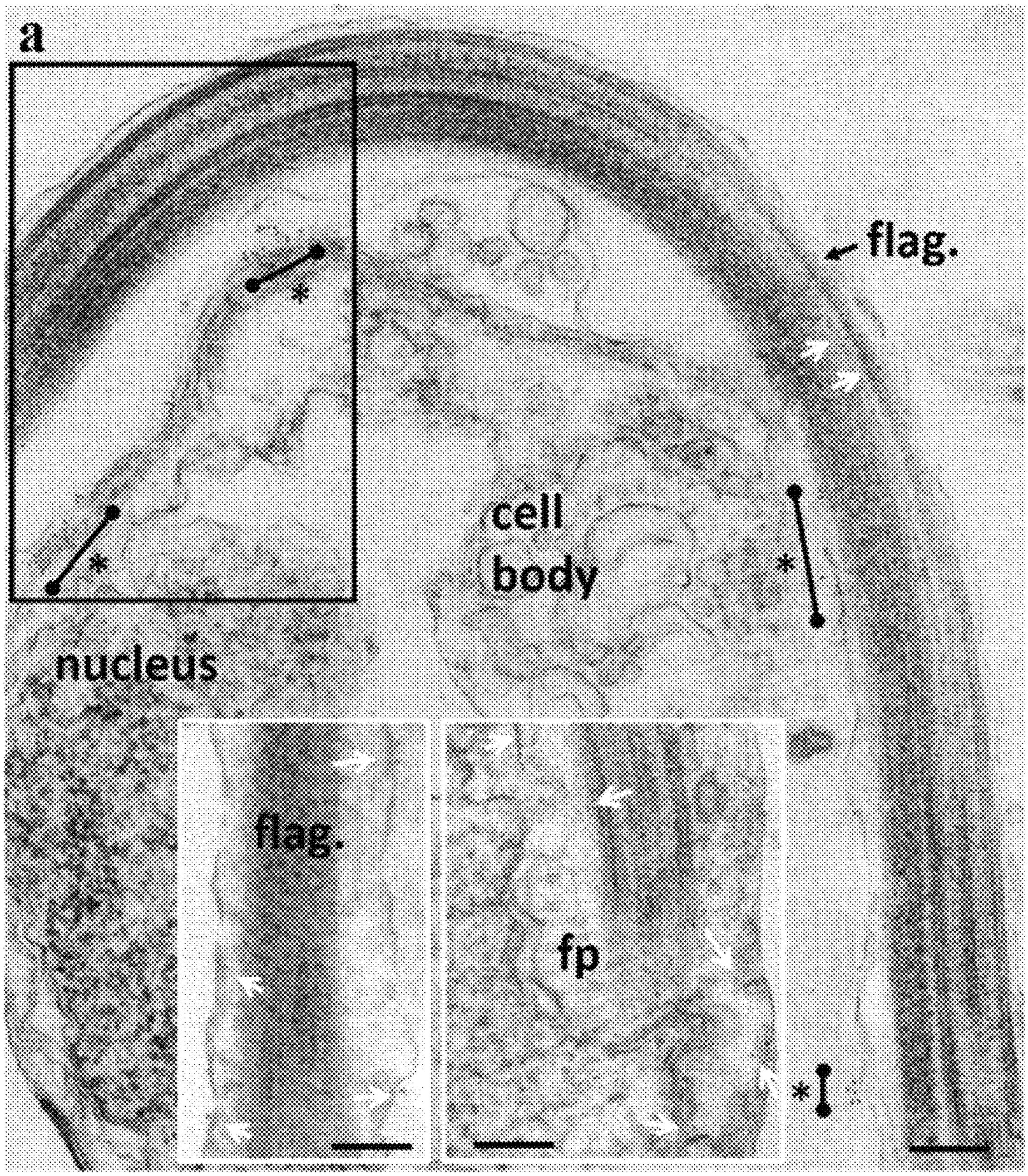
FIG. 5: IFX is expressed on the *T. vivax* flagellum membrane and concentrated at the borders of the flagellum attachment zone. a, Immunogold electron microscopy localised IFX to the flagellum membrane including the flagellar pocket (insets, white arrows). IFX was concentrated in clusters along the length of the flagellum (bars marked *). Gold particles are highlighted in red. b, Zoom of box in a, showing IFX located between the flagellum and cell membranes; another example is shown in c. d, IFX localised to the boundaries of the flagellum attachment zone. flag.=flagellum; fm=flagellar membrane; fp=flagellar pocket; cm=parasite cell membrane; scale bars represent 100 nm.

IFX is a previously undescribed type I cell surface glycoprotein containing a short (18 amino acid) cytoplasmic region. Sequence-based searches showed that IFX did not encode any known protein domains, nor any easily identifiable paralogous or orthologous proteins in other sequenced *Trypanosoma* spp. genomes. To begin the functional characterisation of IFX, we localised the protein to the flagellum membrane, which included the flagellar pocket, of blood-stage parasites using immunogold electron microscopy (FIG. 5*a*). In mid-saggital sections, the protein was enriched at discrete clusters at the points where the flagellar membrane was in close apposition to the cell membrane along the length of the flagellum (FIG. 5*a*); specifically, the gold particles were located between the flagellum and cell membranes (FIG. 5*b, c*). In transverse sections, IFX was enriched at the sites where the flagellar and cellular membranes separated at the borders of the flagellum attachment zone; in different sections, these clusters were either uni- or bilaterally located (FIG. 5*d*). These data suggested IFX was localised to the flagellum membrane and particularly enriched as continuous or punctuated bilateral stripes bordering the FAZ along the length of the flagellum, suggesting a structural role in maintaining flagellar function (Sunter and Gull 2016, Trends Parasitol. 32, 309-324).

Antibodies to IFX Passively Protect

Figure 6:
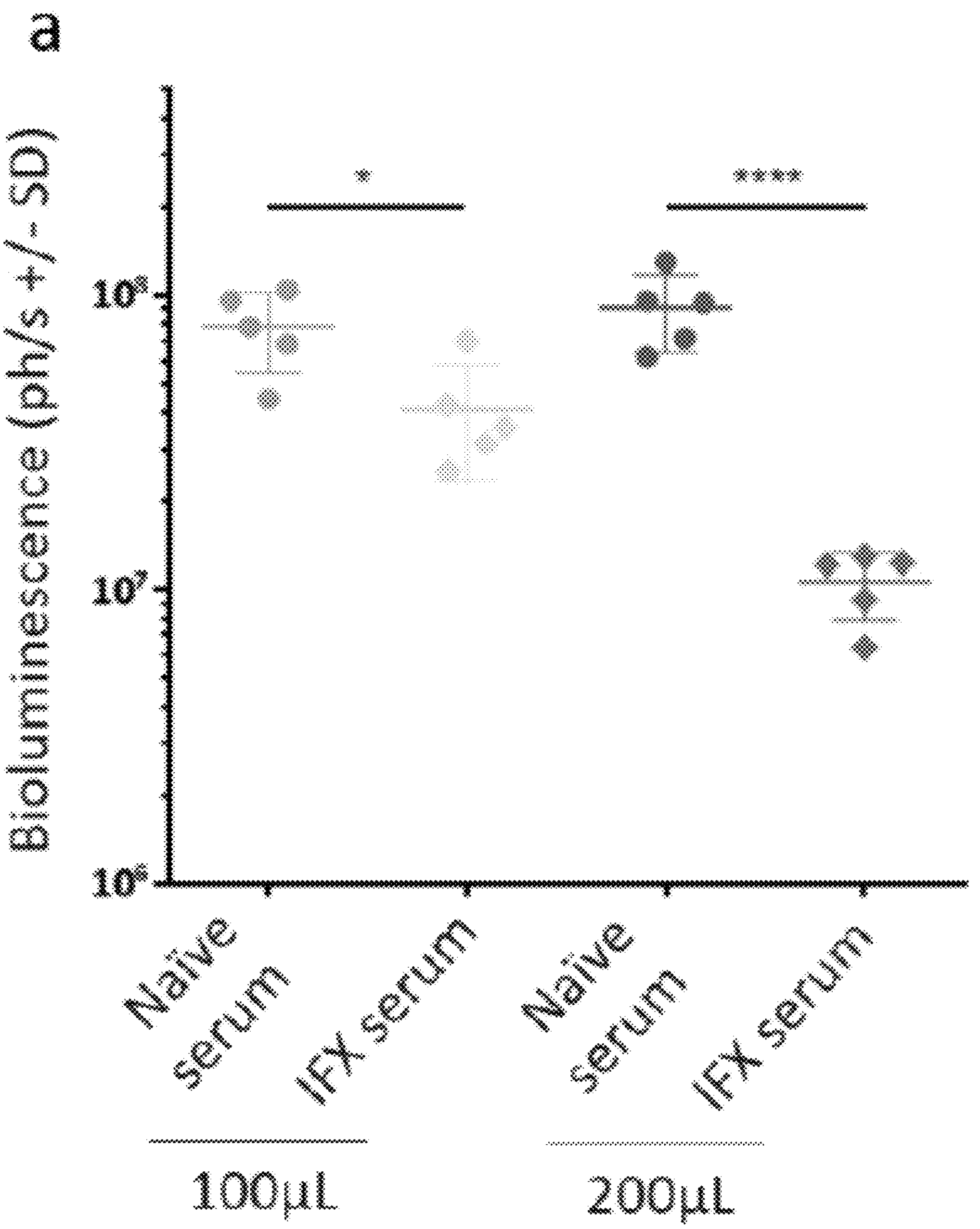
FIG. 6: Passive transfer of immunity to *T. vivax* infections with anti-IFX antibodies. a, Dose-dependent passive protection against *T. vivax* infection by adoptive transfer of sera from IFX-vaccinated mice relative to unimmunised control sera. b, Three of six anti-IFX IgG1 mAbs binding different epitopes each given at a dose of 3×100 μg passively protect against *T. vivax* infection relative to isotype-matched control. c, Passive protection of the IgG1 8E12 mAb is dose dependent. Parasitaemia was quantified at day 5 using bioluminescence; bars indicate mean±SD, groups were compared by student t-test *P≤0.01; P≤0.001; *P≤0.0001; ****P≤0.00001.

To determine the immunological mechanisms of IFX-mediated protection, we first demonstrated that antibodies contributed to immunity by showing that parasite growth was inhibited by transferring serum from vaccinated animals to naïve recipients in a dose-dependent manner (FIG. 6*a*). This was consistent with no loss in protection in vaccinated animals where both CD4-positive and CD8-positive T-lymphocytes and NK cells had been ablated using depleting monoclonal antibodies. To investigate these effects further using an independent approach, we selected a panel of hybridomas secreting monoclonal antibodies (mAbs) to IFX. Out of six mAbs selected, three affected parasite growth when purified and their ability to passively confer protection to *T. vivax* infections in unimmunised mice quantified. (FIG. 6*b*). These protective effects titrated with dose (FIG. 6*c*).

Multiple Mechanisms of Anti-IFX Protection

Figure 7:
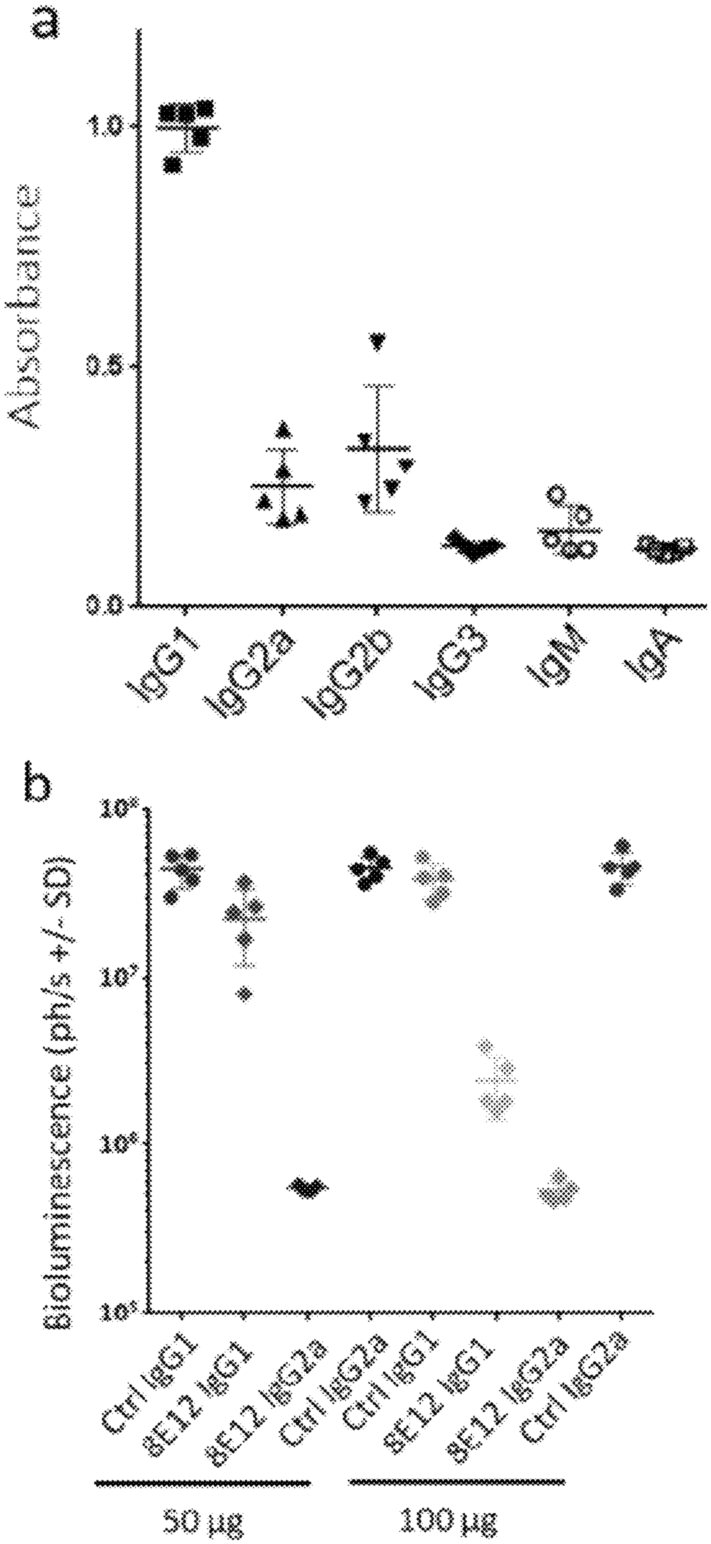
FIG. 7: Multiple mechanisms of antibody-mediated anti-IFX immunological protection dominated by complement recruitment. a, IFX immune serum is dominated by IgG1 isotype antibodies. b, 8E12-IgG2a monoclonal antibodies are far more potent as passive protection than IgG1-8E12 mAbs. c, Dose titration of recombinant anti-IFX mAb 8E12-IgG2a isotype showing potent passive protection against a *T. vivax* infection compared to an isotype-matched control. d, Passive transfer of anti-IFX recombinant 8E12-IgG2a mAbs containing mutations that prevent binding to C1q (ΔC1q), FcRs (ΔFcR) or both (ΔC1qΔFcR) relieved the inhibition of parasite multiplication to differing degrees demonstrating multiple mechanisms of antibody-based immunological protection including a major role for complement. Parasitaemia was quantified at day 5 using bioluminescence; bars indicate mean±SD.

Isotyping the mAbs to IFX revealed that they were all of the IgG1 subclass, which in mice, do not effectively recruit immune effector functions such as complement or bind Fc receptors suggesting that direct antibody binding to IFX affected parasite viability. In addition, isotyping IFX immune serum suggested that the predominant antibody isotype was IgG1, although other isotypes such as IgG2 subclasses were detectable (FIG. 7*a*). To establish the role of Fc-mediated immune effectors in IFX-mediated antibody protection, we selected a mAb, 8E12, that gave intermediate protective effects, and by cloning the rearranged antibody variable regions, switched the mAb isotype from IgG1 to IgG2a. Upon adoptive transfer of 8E12-IgG2a to parasite-challenged mice, we observed a much increased potency compared to the 8E12-IgG1 and titrating this antibody showed that three doses of 50 micrograms or more was sufficient to confer sterile protection (FIG. 7*b*), and this effect could be titrated to 20 micrograms (FIG. 7*c*). This demonstrated that recruitment of antibody-mediated immune effectors were important for immunity and to quantify their relative contributions, we engineered three further mAbs which each lacked the binding sites for C1q (ΔC1q), FcRs (ΔFcR), or both (ΔC1qΔFcR). When used in passive protection experiments, we observed that mutation of the C1q binding site almost completely reversed the inhibition of parasite growth, demonstrating that C1q-mediated complement recruitment was the major mechanism of immunological protection (FIG. 7*d*). Mutating the FcR binding site also relieved the inhibition of parasite growth, but to a much lesser extent, while mutation of both inhibited growth with a similar potency as the IgG1 isotype (FIG. 7*d*). These experiments revealed that anti-IFX antibodies inhibited parasite multiplication by multiple immune mechanisms dominated by the recruitment of complement but also roles for FcR binding and direct binding to IFX.

IFX is Highly Conserved Across Isolates

Figure 8:
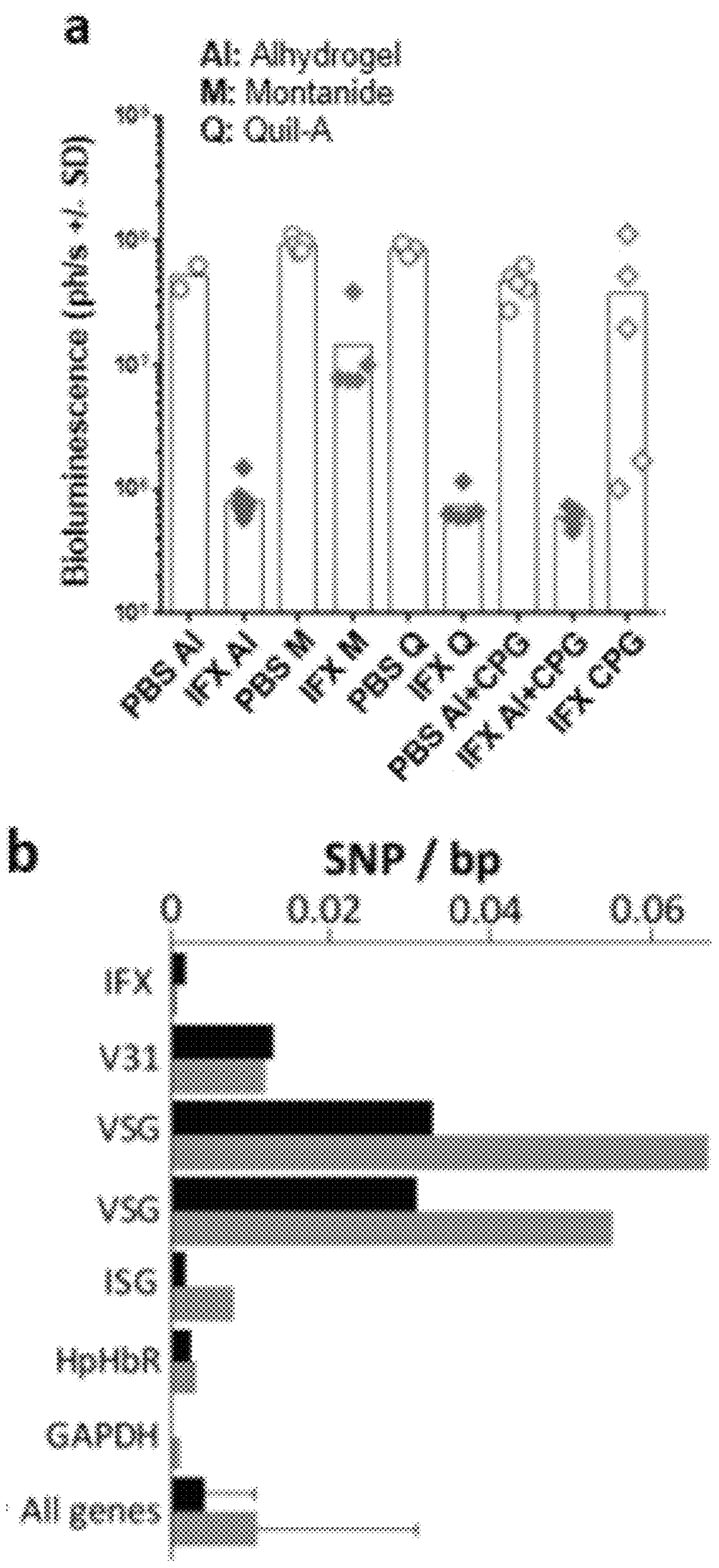
FIG. 8: IFX is highly conserved and can elicit long-lasting immunity to *T. vivax* infections. a, Testing veterinary-approved adjuvants using subcutaneous delivery in mice demonstrates that QuilA and alum with CpG are as effective as alum i.p. b, Population genetic analysis from the genomes of 29 *T. vivax* isolates from different geographical regions show that the gene encoding IFX is highly conserved compared to other genes encoding selected parasite surface proteins (V31, two VSGs, ISG, HpHbR), a housekeeping gene (GAPDH) and all genes for comparison. c, IFX is not immunogenic in the context of a natural infection. Sera from ten naturally-infected cattle from Cameroon (C) and Kenya (K) were tested for the immunoreactivity to the named proteins by ELISA. Naïve controls are UK cattle. Individual data points are shown and the median indicated. d, A group of mice vaccinated with IFX were protected from multiple *T. vivax* challenges including a subcutaneous challenge and over 100 days following the final booster immunisation.

To begin translating these findings towards a vaccine, we next asked whether other adjuvants and routes of administration that are approved for veterinary use could elicit protective immune responses. We selected three adjuvants and used them in a recombinant protein-in-adjuvant formulation by subcutaneous administration. We observed that the adjuvant QuilA but not Montanide or CpG adjuvants were just as effective as alum alone in eliciting protective immune responses (FIG. 8*a*). One potential challenge with subunit vaccines is that the genes encoding antigens eliciting protective immune responses in natural infections can be under diversifying selection potentially leading to strain-specific immunity and thereby limiting the usefulness of the vaccine (Ouattara et al. 2015, Vaccine 33, 7506-7512). We therefore analysed the sequence of the gene encoding IFX from 29 *T. vivax* genomes isolated from representative geographical regions, and, by comparison to other surface antigens showed that it was highly conserved, containing just a single non-synonymous polymorphism in two isolates (FIG. 8*b*). This was supported by the finding that sera from naturally-infected cattle were not immunoreactive to IFX (FIG. 8*c*). Finally, a successful vaccine must be able to elicit long-lasting protection and so we repeatedly challenged vaccinated mice over 100 days after receiving their final immunisation. We observed that mice remained fully protected even to higher doses of parasites which were also delivered subcutaneously (FIG. 8*d*).

Discussion

We have shown that it is possible to elicit sterile immunity to an experimental *Trypanosome* infection by immunising with a recombinant subunit vaccine corresponding to the ectodomain of an invariant cell surface parasite protein termed IFX. The localisation of IFX to the flagellum membrane at the periphery of the FAZ suggests that it performs a crucial role in flagellar structure and function. Our demonstration that antibodies are required for immunity raises important questions about the immunoprotective mechanisms employed by trypanosomes, and importantly, their vulnerabilities that can be exploited to develop vaccines. The inhibition of parasite growth by antibodies to IFX suggest that the parasite's VSG surface coat cannot fully shield it from antibody binding and that anti-IFX antibodies are not removed by endocytosis within the flagellar pocket from the parasite surface with sufficient rapidity to prevent antibody-mediated immune effector recruitment. The fact that sera from infected cattle was not immunoreactive to IFX suggest that natural parasite infections in some species can avoid generation of protective antibody responses. These mechanisms could include perturbations of the B-cell compartment which have been described for other species of *Trypanosome* (Frenkel et al. 2016, PLoS Pathog. 12, e1005733; Radwanska et al. 2008, PLoS Pathog. 4, e1000078; Corsini et al. 1977, Clin. Exp. Immunol. 29, 122-131). The discovery of an antigen that can elicit sterile protection to a *Trypanosome* infection provides optimism and a technical roadmap that could be followed to identify vaccine antigens not just for other *Trypanosome* species, but also parasites that have thus far proved intractable to vaccine development. Finally, IFX represents a very attractive vaccine candidate for an important livestock disease that has been a major barrier to the socioeconomic development of sub-Saharan Africa.

The invention claimed is:

1. A trypanosomal vaccine, comprising:

a protein comprising an amino acid sequence set forth in SEQ ID NO: 1, and one or more adjuvants.

2. The trypanosomal vaccine of claim 1, which is a *Trypanosoma vivax* vaccine.

3. The trypanosomal vaccine of claim 1, wherein said one or more adjuvants comprise a saponin adjuvant.

4. The trypanosomal vaccine of claim 1, which additionally comprises a pharmaceutically acceptable carrier, diluent, excipient, or combination thereof.

5. A method of vaccinating against a trypanosomal infection in a mammal, comprising: administering to the mammal a therapeutically effective amount of the trypanosomal vaccine of claim 1.

6. The method of claim 5, wherein the trypanosomal infection is an infection mediated by *Trypanosoma vivax*.

7. The method of claim 5, wherein the trypanosomal infection is animal African trypanosomiasis (AAT).

8. A method of inducing an immune response in a mammal, wherein the method comprises administering to the mammal an effective amount of the trypanosomal vaccine composition of claim 1.

9. The method of claim 5, wherein the mammal is an ungulate.

10. A kit of parts, comprising: the trypanosomal vaccine of claim 1, a medical instrument or other means for administering the trypanosomal vaccine and instructions for use.

11. The method of claim 9, wherein the ungulate is selected from the group consisting of cattle, goats, sheep, horses, pigs and camels.

12. The method of claim 5, wherein the trypanosomal vaccine is administered by parenteral administration.

13. The method of claim 12, wherein the trypanosomal vaccine is administered intradermally, intramuscularly, intravenously, or subcutaneously.

14. The method of claim 5, wherein the trypanosomal vaccine is administered by epidural or mucosal administration.

15. The method of claim 5, wherein the trypanosomal vaccine is administered by intranasal, oral, pulmonary or rectal administration.

16. The method of claim 8, wherein the trypanosomal vaccine is administered by parenteral administration.

17. The method of claim 16, wherein the trypanosomal vaccine is administered intradermally, intramuscularly, intravenously, or subcutaneously.

18. The method of claim 8, wherein the trypanosomal vaccine is administered by epidural or mucosal administration.

19. The method of claim 8, wherein the trypanosomal vaccine is administered by intranasal, oral, pulmonary or rectal administration.

* * * * *